(12) United States Patent
Yoshikawa et al.

(10) Patent No.: US 11,179,092 B2
(45) Date of Patent: Nov. 23, 2021

(54) INFORMATION PROCESSING APPARATUS AND INFORMATION PROCESSING METHOD

(71) Applicant: SONY CORPORATION, Tokyo (JP)

(72) Inventors: Kiyoshi Yoshikawa, Saitama (JP); Naoya Sazuka, Tokyo (JP); Yoshihiro Wakita, Tokyo (JP)

(73) Assignee: SONY CORPORATION, Tokyo (JP)

( * ) Notice: Subject to any disclaimer, the term of this patent is extended or adjusted under 35 U.S.C. 154(b) by 298 days.

(21) Appl. No.: 16/307,223

(22) PCT Filed: Mar. 31, 2017

(86) PCT No.: PCT/JP2017/013624
§ 371 (c)(1),
(2) Date: Dec. 5, 2018

(87) PCT Pub. No.: WO2017/221504
PCT Pub. Date: Dec. 28, 2017

(65) Prior Publication Data
US 2019/0261910 A1    Aug. 29, 2019

(30) Foreign Application Priority Data

Jun. 20, 2016  (JP) .............................. JP2016-121737

(51) Int. Cl.
*A61B 5/11*    (2006.01)
*A61B 5/00*    (2006.01)
(Continued)

(52) U.S. Cl.
CPC .............. *A61B 5/4035* (2013.01); *A61B 5/05* (2013.01); *A61B 5/11* (2013.01); *A61B 5/16* (2013.01);
(Continued)

(58) Field of Classification Search
None
See application file for complete search history.

(56) References Cited

U.S. PATENT DOCUMENTS

| 8,439,836 | B2 | 5/2013 | Storm |
| 2013/0079602 | A1 | 3/2013 | Picard et al. |
| 2016/0034634 | A9* | 2/2016 | Hong ................... A61B 5/7264 702/19 |

FOREIGN PATENT DOCUMENTS

| AT | 503418 T | 4/2011 |
| AU | 2003228159 A1 | 11/2003 |

(Continued)

OTHER PUBLICATIONS

Benedek, et al., "A Continuous Measure of Phasic Electrodermal Activity", Journal of Neuroscience Methods, Jan. 8, 2010, 80-91 pages.

(Continued)

*Primary Examiner* — Ankit D Tejani
(74) *Attorney, Agent, or Firm* — Chip Law Group

(57) ABSTRACT

An information processing apparatus according to the present technology includes a processing section that executes a process including a correction process of specifying noise included in perspiration data acquired by a perspiration sensor on a basis of sensor data acquired by a different type of sensor than the perspiration sensor, and removing the noise from the perspiration data. According to such a technology, noise estimated according to other sensor data can be removed from the perspiration data, making it possible to maintain high accuracy in a later process of estimating activity in the autonomic nerves.

16 Claims, 21 Drawing Sheets

(51) Int. Cl.
*A61B 5/05* (2021.01)
*A61B 5/16* (2006.01)

(52) U.S. Cl.
CPC .......... *A61B 5/4266* (2013.01); *A61B 5/6801* (2013.01); *A61B 5/721* (2013.01); *A61B 5/7264* (2013.01); *A61B 5/7278* (2013.01); *A61B 2560/0252* (2013.01)

(56) References Cited

FOREIGN PATENT DOCUMENTS

| | | | |
|---|---|---|---|
| CA | 2483903 | A1 | 11/2003 |
| DE | 60336557 | | 5/2011 |
| DK | 1519679 | T3 | 7/2011 |
| EP | 1519679 | A1 | 4/2005 |
| JP | 2005-524464 | A | 8/2005 |
| JP | 2014-076209 | A | 5/2014 |
| JP | 2015-104516 | A | 6/2015 |
| NO | 20022218 | A1 | 11/2003 |
| WO | 2003/094726 | A1 | 11/2003 |
| WO | 2013/044183 | A2 | 3/2013 |

OTHER PUBLICATIONS

Benedek, et al., A Continuous Measure of Phasic Electrodermal Activity, Journal of Neuroscience Methods, Jan. 8, 2010, 81-90 pages.

Benedek, et al., "A Continuous Measure of Phasic Electrodermal Activity", Journal of Neuroscience Methods, vol. 190, Issue 01, 2010, pp. 80-91.

International Search Report and Written Opinion of PCT Application No. PCT/JP2017/013624, dated Jun. 13, 2017, 02 pages of translation and 09 pages of ISRWO.

* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2017/013624 filed on Mar. 31, 2017, which claims priority benefit of Japanese Patent Application No. JP 2016-121737 filed in the Japan Patent Office on Jun. 20, 2016. Each of the above-referenced applications is hereby incorporated herein by reference in its entirety.

TECHNICAL FIELD

The present disclosure relates to an information processing apparatus, an information processing method, and a program.

BACKGROUND ART

Perspiration of a living body mainly is divided into mental perspiration caused by mental or psychological factors such as tension, anxiety, or stress, and thermal perspiration that occurs to maintain body temperature at a suitable temperature. Mental perspiration reflects activity in the sympathetic nerves, such as a high level of tension or arousal in the sympathetic nervous system. For this reason, by measuring mental perspiration, the activity in the autonomic nerves of the living body, particularly the sympathetic nerves, can be estimated.

For example, Non-Patent Literature 1 below discloses a technology for separating data (perspiration data) related to skin conductance responses (SCRs) which change due to perspiration into tonic activity data (corresponding to thermal perspiration) and phasic activity data (corresponding to mental perspiration). With such a technology, the activity in the sympathetic nerves of a living body can be estimated from perspiration data.

CITATION LIST

Non-Patent Literature

Non-Patent Literature 1: Benedek, M., Kaernbach, C., "A continuous measure of phasic electrodermal activity", Journal of Neuroscience Methods, 190, (2010), 80-91.

DISCLOSURE OF INVENTION

Technical Problem

The sites where the mental perspiration described above may occur are limited to the wrists, the armpits, the head, the soles of the feet, and the like. Furthermore, these sites are the sites of relatively large body motion during daily activity. Consequently, the perspiration data acquired from the sites where mental perspiration occurs may include large amounts of noise due to factors such as body motion. If such noise is included in the perspiration data, there is a risk that the accuracy of estimating the activity in the autonomic nerves will be lowered.

Accordingly, the present disclosure proposes a novel and improved information processing apparatus, information processing method, and program capable of maintaining high estimation accuracy of the activity in the autonomic nerves.

Solution to Problem

According to the present disclosure, there is provided an information processing apparatus including: a processing section that executes a process including a correction process of specifying noise included in perspiration data acquired by a perspiration sensor on a basis of sensor data acquired by a different type of sensor than the perspiration sensor, and removing the noise from the perspiration data.

Also, according to the present disclosure, there is provided an information processing method, executed by a processor, including: acquiring perspiration data acquired by a perspiration sensor; and specifying noise included in the perspiration data on a basis of sensor data acquired by a different type of sensor than the perspiration sensor, and removing the noise from the perspiration data.

Also, according to the present disclosure, there is provided a program causing a computer to function as: a processing section that executes a process including a correction process of specifying noise included in perspiration data acquired by a perspiration sensor on a basis of sensor data acquired by a different type of sensor than the perspiration sensor, and removing the noise from the perspiration data.

Advantageous Effects of Invention

According to the present disclosure as described above, it is possible to maintain high estimation accuracy of the activity in the autonomic nerves.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is a diagram for explaining an overview of an information processing system according to an embodiment of the present disclosure.

FIG. 2 is an outline diagram illustrating an example of sites where mental perspiration occurs.

FIG. 3 is a block diagram illustrating an exemplary configuration of an information processing system according to the embodiment.

FIG. 4 is a diagram illustrating an example of temperature sensor data generated by a temperature sensor used as an environmental sensor.

FIG. 5 is a block diagram illustrating an exemplary functional configuration of a control section according to the embodiment.

FIG. 6 is an example of a graph illustrating time-series change of measurement values measured by a perspiration sensor and an acceleration sensor.

FIG. 7 is a graph illustrating uncorrected perspiration data.

FIG. 8 is a graph illustrating corrected perspiration data.

FIG. 9 is a graph illustrating an example of an extraction result of mental perspiration data and thermal perspiration data extracted by an extraction section according to the embodiment.

FIGS. 10A and 10B are diagrams for explaining an example of a sympathetic nerve estimation method based a time-series distribution of mental perspiration data.

MODE(S) FOR CARRYING OUT THE INVENTION

Figure 1:
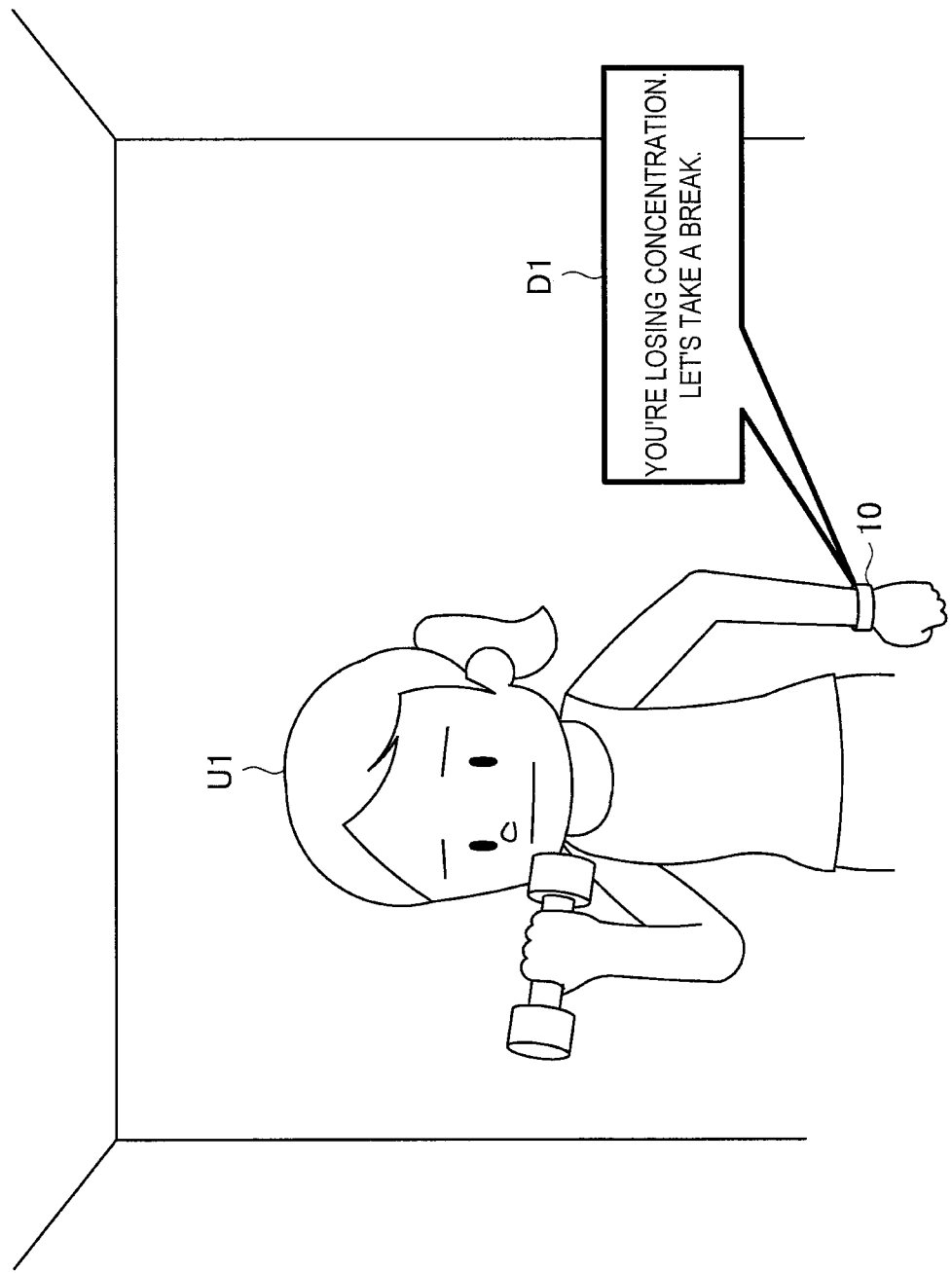
[FIG. 1]

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.

1. Overview of system
2. Information processing system according to present embodiment
   2.1. Exemplary system configuration and exemplary apparatus configuration
   2.2. Configuration and function of control section
   2.3. Process flow
3. Applied examples
3.1. Using to improve work efficiency
3.2. Detecting sleepiness and imparting stimulus
3.3. Model sharing
4. Exemplary hardware configuration
5. Conclusion <<1. Overview of System>>

FIG. 1 is a diagram for explaining an overview of an information processing system according to an embodiment of the present disclosure. In the information processing system according to the present embodiment, for example, as illustrated in FIG. 1, a wristwatch-style device 10 may be worn on or attached to a wrist or the like of a user U1 (one example of an individual). The wristwatch-style device 10 is an example of the information processing apparatus 10 described later. The information processing system uses perspiration data regarding the skin of the user U1 acquired by a perspiration sensor provided in the wristwatch-style device 10 to estimate the activity in the autonomic nerves of the user U1, particularly the activity in the sympathetic nerves. Also, on the basis of an estimation result of the activity in the autonomic nerves, the information processing system may output content like that stated in the presentation D1 to the user U1 in a variety of modes (for example, by display, stimulus, sound, or a combination of these). With this arrangement, the user U1 is able to know about the activity in one's own autonomic nerves, such as one's concentration or wakefulness.

Such an information processing system may be applied to situations or activities that demand knowledge of the user's concentration or wakefulness. For example, as illustrated in FIG. 1, the information processing system may be used to check the sustained concentration of the user U1 who is exercising. With this arrangement, the efficiency of the training effects from the exercise performed by the user U1 can be improved. In addition, the information processing system may also be applied to workers who carry out work requiring concentration, or work that compels one to stay awake over a long period of time. Specifically, the information processing system may also be applied to workers who carry out work that demands thinking, such as studying or desk work, or work that demands safety and concentration, such as freight transport or working at heights.

Also, the mode of the information processing apparatus 10 included in the information processing system is not particularly limited. Although described later in detail, insofar as perspiration data related to mental perspiration is acquirable, the information processing apparatus 10 according to the present embodiment is not limited to a wristwatch-style device 10 like the one illustrated in FIG. 1 for example, and may be realized in any mode.

Generally, the autonomic nerves include the two nervous systems of the sympathetic nerves and the parasympathetic nerves. Examples of responses to states of activity in such autonomic nerves are illustrated in Table 1 below. Among the effectors illustrated below, by measuring the states of the effectors or secretions secreted from the effectors, such as the pupils, salivary glands, blood pressure, or heart rate, it is possible to estimate to some degree the activity in the autonomic nerves (for example, the degree to which the sympathetic nerves are dominant)

TABLE 1

| | Effector | Sympathetic Nerves | Parasympathetic Nerves |
|---|---|---|---|
| | Pupils | Dilated | Constricted |
| | Salivary Glands | Small Amount (thick) | Large Amount (thin) |
| | Bronchial Tube | Expanded | Contracted |
| | Respiratory Secretions | Decreased | Increased |
| | Blood Pressure | Increased | Decreased (slightly) |
| | Heart Rate | Increased | Decreased |
| | Liver | Glycogen Breakdown | Glycogen Synthesis |
| Digestive Tract | Movement | Reduced | Improved |
| | Secretions | Decreased | Increased |
| Skin | Blood Vessels | Contracted | — |
| | Pilomotor Muscles | Contracted | — |

TABLE 1-continued

| Effector | Sympathetic Nerves | Parasympathetic Nerves |
| --- | --- | --- |
| Sweat Glands | Increased Perspiration | — |

Among these, it is known that in the sweat glands of the skin, dominance of the sympathetic nerves causes an increase in the amount of perspiration. Such perspiration is also called mental perspiration. Mental perspiration is perspiration discharged from the eccrine glands when the sympathetic nerves enter a dominant state because of mental or psychological factors, such as stress, tension, or anxiety. In other words, mental perspiration reflects the activity in the sympathetic nerves, such as a high level of tension or arousal in the sympathetic nervous system.

Note that typically, perspiration discharged to adjust body temperature is called thermal perspiration. Thermal perspiration is unrelated to the activity in the autonomic nerves, and is perspiration caused by the thermoregulatory center in the hypothalamus to adjust the body temperature of a living body. Table 2 below illustrates categorized differences between mental perspiration and thermal perspiration.

TABLE 2

|  | Mental Perspiration | Thermal Perspiration |
| --- | --- | --- |
| Perspiration Site | Localized sites such as palms, head, soles of feet, and armpits | Skin all over body |
| Perspiration Stimulus | Mental stimuli (tension, stress, concentration) | Thermal stimuli (thermoregulation) |
| Perspiration Amount | Slight amount | Large amount |
| Perspiration Latency | Short | Long |

First, compared to thermal perspiration, mental perspiration has a short perspiration latency (the time from imparting some kind of stimulus to the living body until perspiration occurs). Also, mental perspiration is known to have a shorter latency than the reactions by the other effectors illustrated in Table 1. Consequently, by measuring mental perspiration, it becomes possible to estimate the activity in the autonomic nerves more rapidly than measuring the reactions (such as blood pressure, for example) by other effectors. In other words, it becomes possible for the activity in the autonomic nerves to be reflected in real time.

On the other hand, whereas thermal perspiration may occur in skin all over the body basically, mental perspiration may occur at localized sites such as the hands (wrists, fingers, palms, and the like), the head, the soles of the feet, or the armpits. Also, the amount of perspiration due to mental perspiration is slight. For this reason, in the case of wanting to detect mental perspiration using a perspiration sensor described later, it is demanded to put the perspiration sensor in contact with such sites. In other words, the information processing apparatus 10 according to the present embodiment preferably is worn on or attached to the sites described above.

Figure 2:
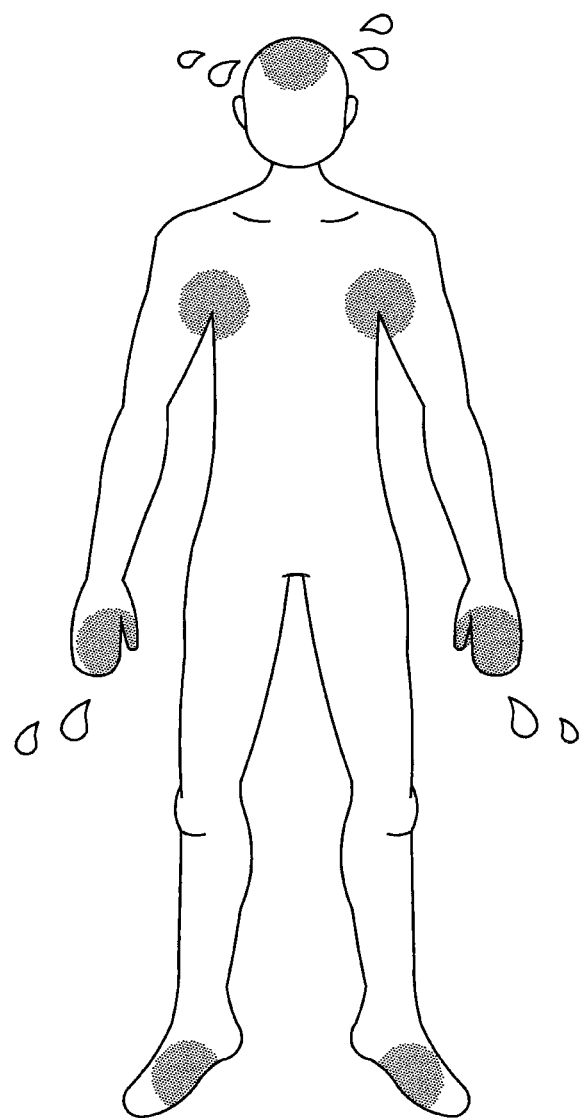
[FIG. 2]

FIG. 2 is an outline diagram illustrating an example of sites where mental perspiration occurs. As described above, mental perspiration on the human body for example may occur at localized sites such as the hands, the head, the soles of the feet, or the armpits. Consequently, the information processing apparatus 10 according to the present embodiment preferably is realized in a mode that is worn on or attached to these sites.

For example, the information processing apparatus 10 may be realized in a mode that is wearable on a part of a user's hand, such as a wristband, a glove, an activity meter, a smartwatch, or a ring. Also, in the case in which the information processing apparatus 10 is attached to the hands, the information processing apparatus 10 may also be a configuration provided in an object associated with work performed by the user, for example Specifically, the information processing apparatus 10 may also be provided on the surface of or inside an object that make come into contact with the hands, such as a mobile terminal, a smartphone, a tablet, a mouse, a keyboard, a handle, a lever, a camera, a piece of exercise equipment (such as a golf club, a tennis racket, or archery gear), a writing instrument, or the like.

In addition, the information processing apparatus 10 may also be realized in a mode that is attachable to an object worn on a part of the user's head, such as a hat, a hair band (headband), an accessory, goggles, or glasses. Also, the information processing apparatus 10 may be provided in a garment such as sportswear, socks, protective gear, shoes, or the like. In this case, the information processing apparatus 10 may be provided in the portions of the garment or shoes that may adhere to the armpits or the soles of the feet of the user.

In other words, insofar as the information processing apparatus 10 is provided to be contactable with a site where the mental perspiration described above occurs, the mode in which the information processing apparatus 10 is realized is not particularly limited. According to such an information processing apparatus 10, perspiration data mainly caused by mental perspiration can be acquired by the perspiration sensor.

However, in many cases, the perspiration data acquired by the perspiration sensor contains a mixture of perspiration data caused by mental perspiration and perspiration data caused by thermal perspiration. To estimate the activity in the autonomic nerves of a living body accurately, the extraction of perspiration data related to mental perspiration from the perspiration data is demanded.

For example, Non-Patent Literature 1 described above (Benedek, M., Kaernbach, C., "A continuous measure of phasic electrodermal activity", Journal of Neuroscience Methods, 190, (2010), 80-91) discloses a technology for separating data (perspiration data) related to skin conductance responses (SCRs) which change due to perspiration into tonic activity data (corresponding to thermal perspiration) and phasic activity data (corresponding to mental perspiration). With this arrangement, it becomes possible to extract perspiration data related to mental perspiration from the perspiration data.

However, at the above-described sites where mental perspiration occurs, such as the head, the armpits, the hands, and the soles of the feet, body motion readily influences the measurement by the perspiration sensor. In other words, the perspiration data acquired at the sites may include large amounts of noise. It is difficult to extract perspiration data related to the mental perspiration accurately from perspiration data that includes such noise. Consequently, if such noise is included in the perspiration data, there is a risk that the accuracy of estimating the activity in the autonomic nerves will be lowered.

Accordingly, the information processing system according to the present embodiment removes the noise included in the perspiration data and corrects the perspiration data, thereby making it possible to improve the accuracy of estimating the activity in the autonomic nerves. Specifically, the information processing system according to the present embodiment removes noise included in the perspiration data on the basis of sensor data acquired by a different type of sensor than the perspiration sensor.

However, it is difficult to specify noise included in perspiration data from the perspiration data alone. Accordingly, at least one type of sensor data different from perspiration data is used. With this arrangement, since it is possible to specify disturbances imparted to the perspiration sensor, noise included in the perspiration data can be specified.

The above describes an overview of the information processing system according to the present embodiment.

<<2. Information Processing System According to Present Embodiment>>

<2.1. Exemplary System Configuration and Exemplary Apparatus Configuration>

Figure 3:
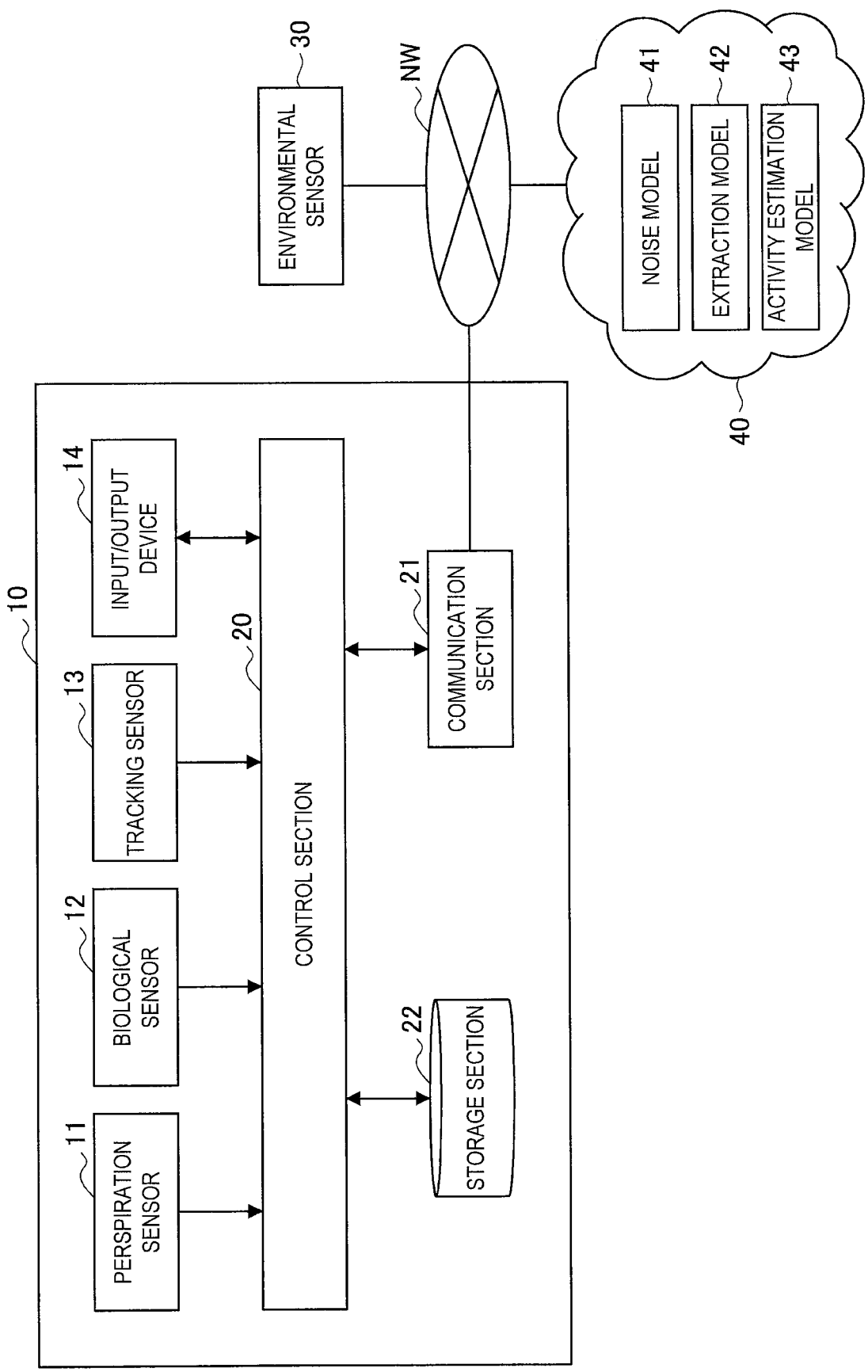
[FIG. 3]

Next, an exemplary configuration of an information processing system 1 according to an embodiment of the present disclosure will be described. FIG. 3 is a block diagram illustrating an exemplary configuration of the information processing system 1 according to the present embodiment. Referring to FIG. 3, the information processing system 1 according to the present embodiment includes the information processing apparatus 10, an environmental sensor 30, and a server 40.

(Information Processing Apparatus)

The information processing apparatus 10 is an example of an apparatus worn on or attached to a user. In FIG. 1, a wristwatch-style device 10 is illustrated as an example of the information processing apparatus 10, but as described above, the information processing apparatus 10 may be realized in a variety of modes. The information processing apparatus 10 may include a processing circuit, a storage apparatus, a communication apparatus, an input/output apparatus, and the like. Also, the information processing apparatus may include various sensors.

Referring to FIG. 3, the information processing apparatus 10 according to the present embodiment is provided with a perspiration sensor 11, a biological sensor 12, a tracking sensor 13, an input/output device 14, a control section 20, a communication section 21, and a storage section 22.

(Perspiration Sensor)

The perspiration sensor 11 is a sensor that detects sweat secreted from the sweat glands (eccrine glands) of the skin. Sweat causes skin to conduct electricity more readily. Consequently, by acquiring the electrodermal activity (EDA) of the skin, sweat can be detected. The perspiration sensor 11 generates perspiration data on the basis of the acquired EDA. The generated perspiration data is output to the control section 20. The perspiration sensor 11 according to the present embodiment may pass a weak current to the skin to measure an electrical resistance value, and compute the skin conductance activity (SCA) as the inverse of the electrical resistance value. In other words, the SCA becomes perspiration data. Note that the perspiration sensor 11 is not limited to being a sensor that computes the SCA, and may also be a sensor that computes skin potential activity (SPA).

For example, the perspiration sensor 11 may be provided near the surface of a housing that houses the information processing apparatus 10. With this arrangement, since the perspiration sensor 11 comes into close contact with the skin, perspiration data can be generated continuously. Since such a perspiration sensor 11 is non-invasive, there is little burden on the person being measured, that is, the user. However, the perspiration sensor 11 may also be embedded under the user's skin or the like in advance. In addition, since the power consumption of the perspiration sensor 11 is relatively small, it is possible to use the perspiration sensor 11 over a long period of time. Also, since the sampling rate of the perspiration sensor 11 is lower (approximately several Hz) than other sensors, the load related to processing the acquired perspiration data is small.

(Biological Sensor)

The biological sensor 12 is one example of a different type of sensor than the perspiration sensor 11, in which the biological sensor 12 is worn on or attached to an individual, detects a state (biological information) regarding the living body of the user, excluding perspiration, and generates biological data. For example, the biological sensor 12 may be a pulse wave sensor, a heart rate sensor, a blood pressure sensor, a body temperature sensor, or the like. By such a biological sensor 12, it is possible to acquire biological data regarding the biological state of the user, in addition to perspiration data. One or more of these biological sensors 12 may be provided in the information processing apparatus 10. The biological data generated by the biological sensor 12 is output to the control section 20.

(Tracking Sensor)

The tracking sensor 13 is an example of a different type of sensor than the perspiration sensor 11, in which the tracking sensor 13 is worn on or attached to an individual, detects motion such as the body motion or movement of the user, and generates tracking data. For example, the tracking sensor 13 may be an acceleration sensor, a gyro sensor, a barometric pressure sensor, a geomagnetic sensor, a global navigation satellite system (GNSS) receiver module, or the like. By such a tracking sensor 13, it is possible to acquire tracking data regarding the motion of the user, in addition to perspiration data. One or more of these tracking sensors 13 may be provided in the information processing apparatus 10. The tracking data generated by the tracking sensor 13 is output to the control section 20.

Note that only one of biological sensor 12 and the tracking sensor 13 described above may be provided in the information processing apparatus 10, or both may be provided in the information processing apparatus 10.

(Input/Output Device)

The input/output device 14 is an apparatus that has a function of acting as an input apparatus and an output apparatus. The input/output device 14 includes a function of outputting in a predetermined mode according to information output from the control section 20, and/or a function of receiving input from the user or the like. In the block diagram illustrated in FIG. 3, an input/output device 14 integrating the input function and the output function is provided in the information processing apparatus 10, but the input/output device 14 may also be realized by a configuration in which the input function and the output function are independent from each other.

The input function exhibited by the input/output device 14 may be realized by an apparatus that receives physical operations by an operating body, speech, gestures, or the like. For example, as a means of exhibiting the input function of the input/output device 14, the input/output device 14 may be realized by a touch panel, a button, a keyboard, a pointing stick, a trackball, a trackpad, an acceleration sensor, a gyro sensor, a camera, an LED sensor, a microphone, or the like. Also, the output function exhibited by the input/output device 14 may be realized by an apparatus capable of outputting in a mode that is perceived by the sense of sight, hearing, touch, or the like. For example, as a means of exhibiting the output function of the input/output device 14, the input/output device 14 may be realized by a display (including a touch panel), a light source such as an LED, a vibrator, an electrode (for imparting an electrical stimulus), a speaker, or the like.

(Control Section)

Figure 5:
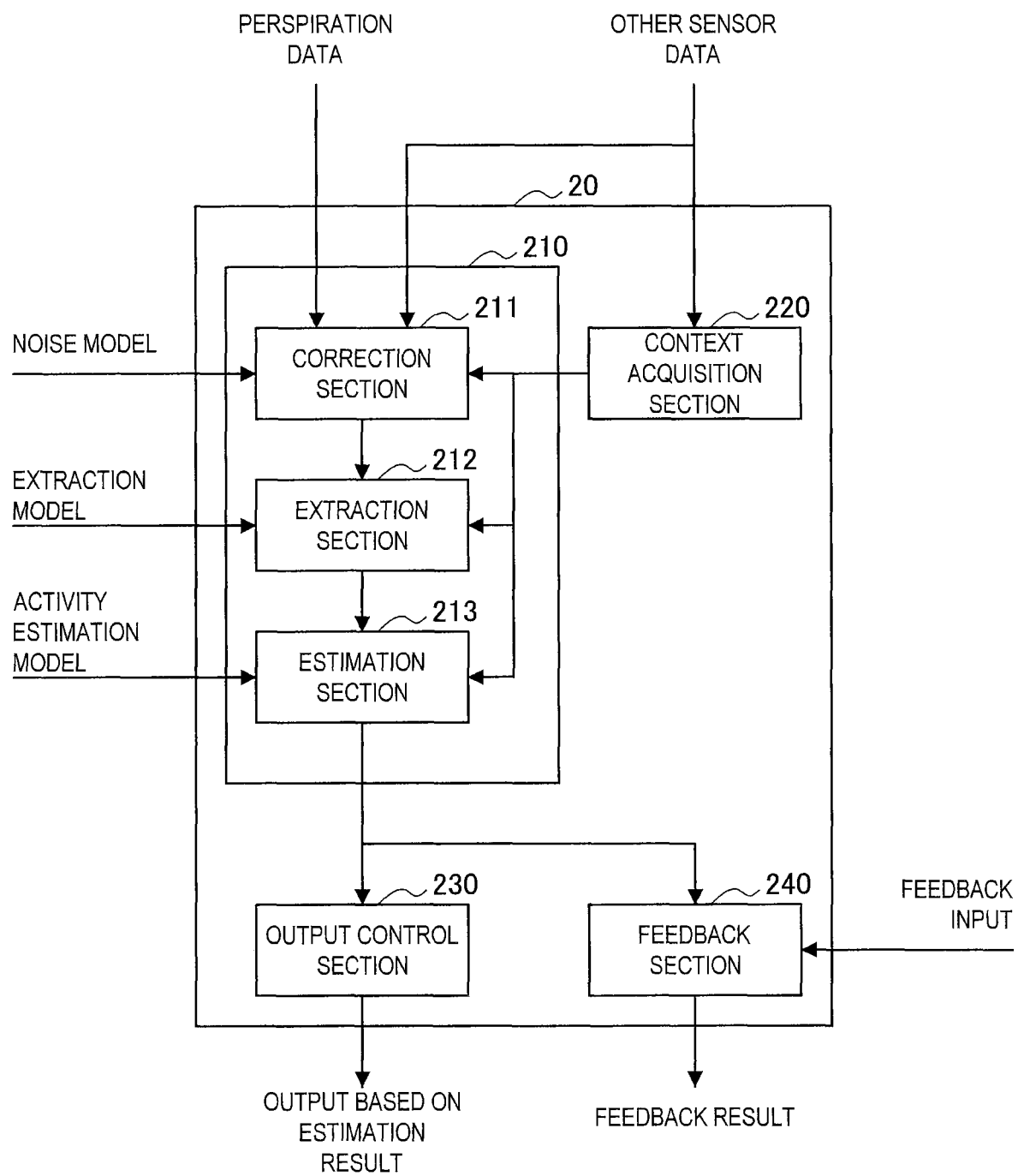
[FIG. 5]

The control section 20 controls the overall operation of the information processing apparatus 10 according to the present embodiment. The function of the control section 20 is realized by a processing circuit such as a central processing unit (CPU) provided in the information processing apparatus 10. Also, as illustrated in FIG. 5 cited later, the control section 20 includes each function of a processing section 210, a context acquisition section 220, an output control section 230, and a feedback section 240, and leads the execution of the operations of the information processing apparatus 10 according to the present embodiment. The function of each of the functional sections included in the control section 20 will be described later.

(Communication Section)

The communication section 21 is a communication means provided in the information processing apparatus 10, and executes various types of wired or wireless communication with external apparatus over a network (or directly). The function of the communication section 21 is realized by a communication apparatus provided in the information processing apparatus 10. For example, the communication section 21 communicates with the environmental sensor 30 and the server 40 over a network NW. With this arrangement, environmental sensor data generated by the environmental sensor 30 and various models stored in the server 40 can be acquired. Additionally, the communication section 21 may also communicate with other apparatus not illustrated in FIG. 3.

(Storage Section)

The storage section 22 is a storage means provided in the information processing apparatus 10, and stores information acquired by the communication section 21, information obtained by each functional section of the control section 20, and the like. For example, the storage section 22 may store various models stored in the server 40. Also, the storage section 22 outputs stored information in response to requests from each functional section of the control section 20 or the communication section 21.

The above describes each functional section and apparatus included in the information processing apparatus 10.

(Environmental Sensor)

The environmental sensor 30 is an example of a sensor that acquires environmental information regarding a predetermined space with a different type of sensor than the perspiration sensor 11. The environmental sensor 30 according to the present embodiment is a sensor that is provided at any position in a space where the user exists, detects a state regarding the environment of the space, and generates environmental sensor data. The environmental sensor data generated by the environmental sensor 30 is output to the information processing apparatus 10 over the network NW (or directly).

Figure 4:
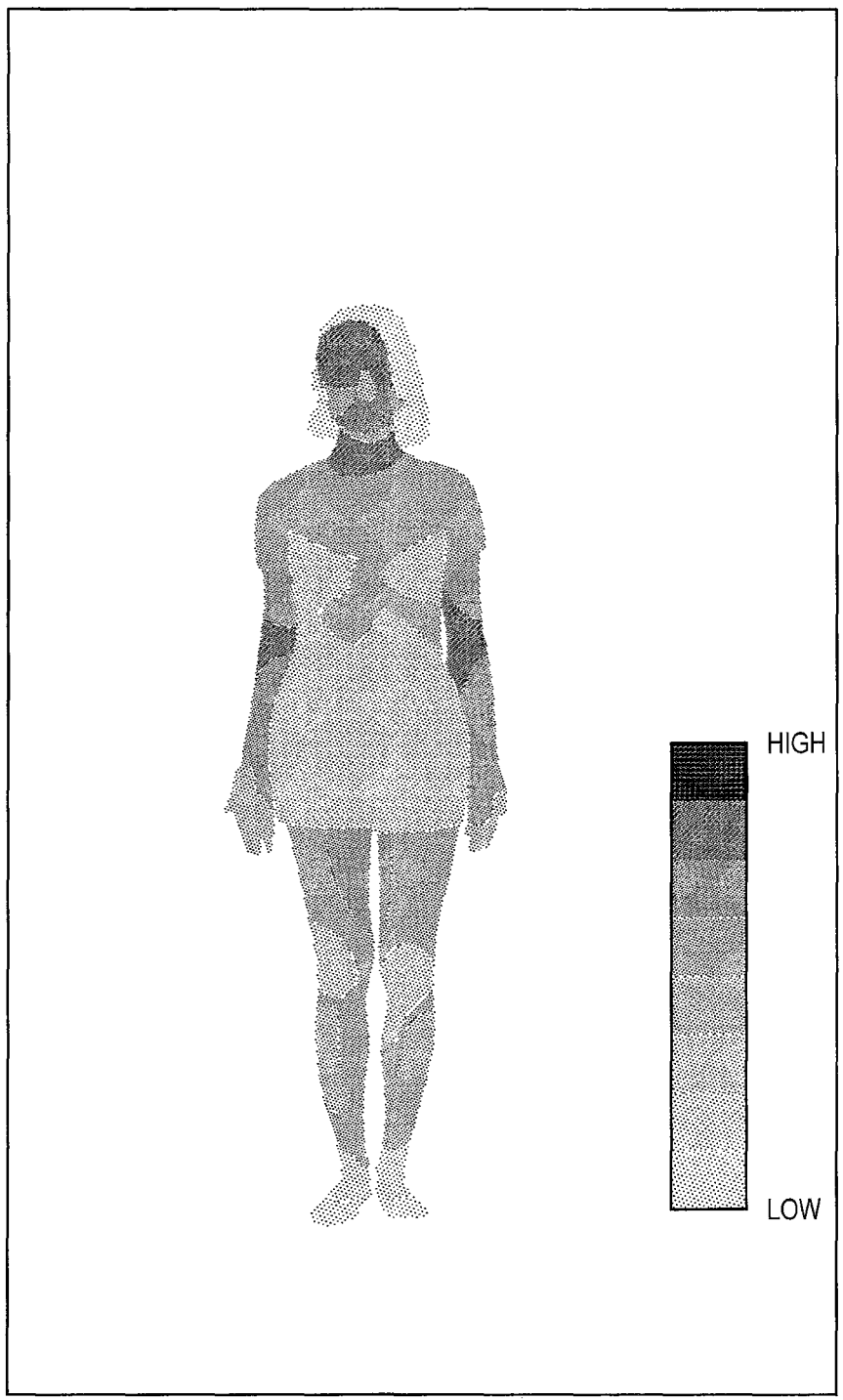
[FIG. 4]

For example, the environmental sensor 30 may be a temperature sensor, a humidity sensor, a barometric pressure sensor, a presence sensor, an illuminance sensor, or a sound sensor (microphone). FIG. 4 is a diagram illustrating an example of temperature sensor data generated by a temperature sensor used as the environmental sensor 30. As illustrated in FIG. 4, the temperature sensor used as the environmental sensor 30 may not only simply measure the air temperature inside a predetermined space, but also acquire a distribution of temperatures of a predetermined target (thermography) as the sensor data. With this arrangement, for example, the temperature at each site of the user's body can be acquired in detail. By so doing, although described later in detail, further improvement of the accuracy of processes such as perspiration data correction becomes possible.

Additionally, the environmental sensor 30 may also be a sensor used in what is called Internet of Things (IoT) equipment. For example, the environmental sensor 30 may also be a sensor that senses the open/closed state or locked state of a door or a window, authentication equipment used for attendance management and such, or the like. In this case, the environmental sensor data output from the environmental sensor 30 may be data indicating the open/closed state or locked state, or alternatively, the authentication result, or the like.

Otherwise, the environmental sensor 30 may also be any of various sensors or apparatus capable of sensing that are provided externally to the information processing apparatus 10 in a situation where the information processing system according to the present embodiment is applied. For example, in the case in which the system is used for transportation equipment such as an automobile, the environmental sensor 30 may also be a speedometer, tachometer, a brake output meter, a potentiometer provided in a drive recorder or the steering wheel, or the like.

(Server)

The server 40 includes one or multiple information processing apparatus on a network. The information processing apparatus included in the server 40 may include a processing circuit, a storage apparatus, and a communication apparatus. FIG. 3 illustrates an example in which the server 40 is realized by a server cluster illustrated in a cloud configuration, but the server 40 may also be realized by a specific server. The server 40 stores various models of a noise model 41, an extraction model 42, and an activity estimation model 43. These models may be used in each process by the processing section 210 described later. The server 40 may output various models to the information processing apparatus 10 in response to instructions from the information processing apparatus 10, and additionally, may also acquire various models updated or newly generated by the information processing apparatus 10.

Note that the various models stored in the server 40 may also be stored in the storage section 22 of the information processing apparatus 10.

<2.2. Configuration and Function of Control Section>

Next, the configuration and function of the control section 20 will be described. FIG. 5 is a block diagram illustrating an exemplary functional configuration of the control section 20 according to the present embodiment. Referring to FIG. 5, the control section 20 is provided with the processing section 210, the context acquisition section 220, the output control section 230, and the feedback section 240.

(Processing Section)

The processing section 210 includes a function of executing a process of estimating the activity in the sympathetic nerves, on the basis of acquired perspiration data. Mainly, the processing section 210 according to the present embodiment executes a correction process that removes noise from perspiration data, an extraction process that extracts data related to mental perspiration (mental perspiration data) from perspiration data, and a state estimation process that estimates the activity in the sympathetic nerves from the extracted mental perspiration data. As illustrated in FIG. 5, these processes are executed by the functions of each component included in the processing section 210, namely a correction section 211, an extraction section 212, and an estimation section 213. Hereinafter, the functions of the correction section 211, the extraction section 212, and the estimation section 213 will be described.

(Correction Section)

The correction section 211 includes a function of correcting perspiration data by removing noise included in the perspiration data. Specifically, the correction section 211 executes a correction process that specifies noise included in the perspiration data on the basis of sensor data acquired by a different type of sensor than the perspiration sensor 11, and removes the noise from the perspiration data. Herein, the different type of sensor means the biological sensor 12, the tracking sensor 13, or the environmental sensor 30 illustrated in FIG. 3. Also, the sensor data means measurement values or the like measured by these sensors.

As described above, the sites where mental perspiration occurs are sites of large body motion, such as the hands and the soles of the feet. For this reason, perspiration data acquired by the perspiration sensor 11 worn on or attached to the sites may include large amounts of noise due to the influence of body motion, skin deformation, and the like. However, it is difficult to specify such noise by obtaining only the time-series change of the perspiration data.

Accordingly, the correction section 211 according to the present embodiment removes noise in the perspiration data by specifying a disturbance which may be a cause of noise and which may occur because of the state or motion of the body, on the basis of sensor data acquired by types of sensors other than the perspiration sensor 11 (for example, the biological sensor 12, the tracking sensor 13, and the environmental sensor 30). By specifying a disturbance from other sensor data, noise that conceivably has occurred in the perspiration data can be specified, and such noise can be removed. With this arrangement, the accuracy of the perspiration data can be improved.

Figure 6:
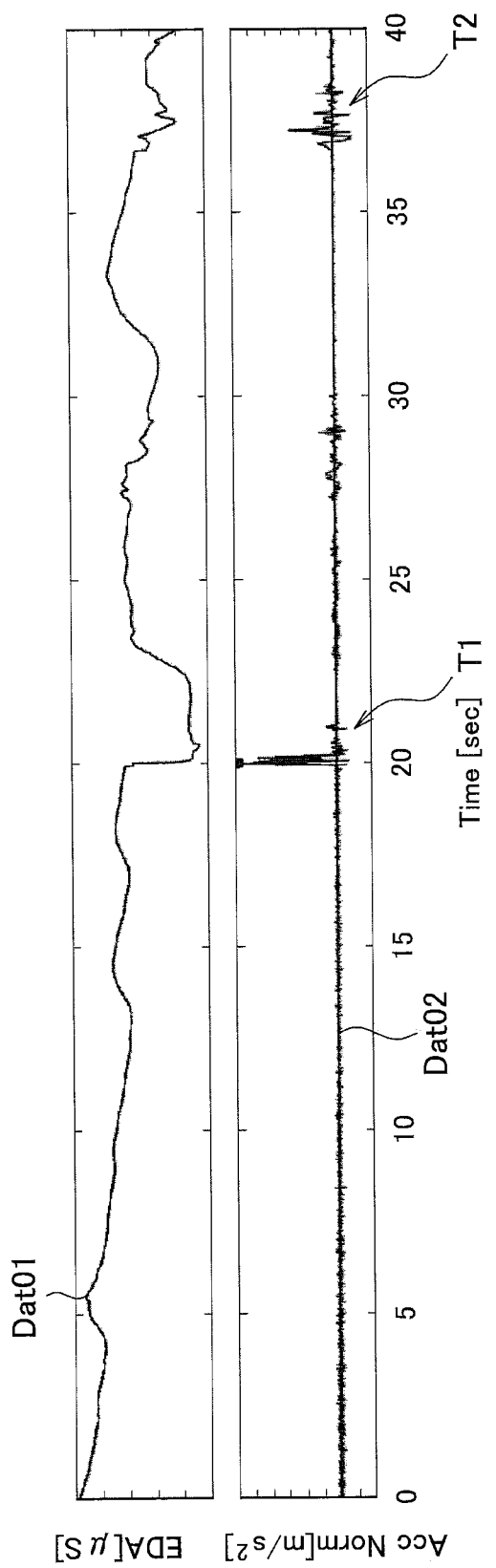
[FIG. 6]

First, the correction section 211 executes a process of specifying noise included in the perspiration data. Hereinafter, one example of specifying noise included in perspiration data will be described. Here, a perspiration sensor and an acceleration sensor (one example of the tracking sensor 13) are worn on the wrist of the person being measured, and the results of acquiring measurement values measured by each sensor in a time series are illustrated. FIG. 6 is an example of a graph illustrating time-series change of measurement values measured by the perspiration sensor and the acceleration sensor. The graph Dat01 illustrated in FIG. 6 is a graph illustrating the time-series change of an EDA (one example of perspiration data) (units: µS) measurement value, while the graph Dat02 is a graph illustrating the time-series change of an acceleration (units: m/s$^2$) measurement value measured by the acceleration sensor at the same time as the perspiration data. The horizontal axis represents time (units: sec).

Referring to the graph Dat02 in FIG. 6, at a time T1, a sudden change in the acceleration measurement value is observed. Also, at a time T2 as well, an oscillation in the measurement value of the acceleration is observed, although the change is smaller than the change in the measurement value at the time T1. These changes in the measurement value occur because the person being measured has moved one's arm. Additionally, at the times T1 and T2, the occurrence of a sudden change and an oscillation of the measurement value in the graph Dat01 is also demonstrated. For example, at the time T1, a sudden drop in the measurement value of the EDA is demonstrated. This drop in the measurement value is thought to be because of poor contact between the perspiration sensor the skin of the person being measured due to the movement of the arm. A similar factor is also conceivable at the time T2. Consequently, at the times T1 and T2, the inclusion of large amounts of noise in the perspiration data is inferred.

In this way, by using sensor data acquired by another sensor other than the perspiration sensor 11, noise included in the perspiration data can be specified. In the example described above, an acceleration sensor is used as the other sensor, but it is also possible to use at least one of the biological sensor 12, the tracking sensor 13, and the environmental sensor 30 illustrated in FIG. 3.

Subsequently, the correction section 211 executes a process of removing the specified noise from the perspiration data to correct the perspiration data. Note that "removing noise" means removing noise that indicates a positive or negative value superimposed onto the true perspiration data. With this arrangement, perspiration data with the noise removed (corrected perspiration data) can be obtained.

For example, the correction section 211 according to the present embodiment may execute a correction process that specifies noise in the perspiration data using the noise model 41, and removes the noise. Here, the noise model 41 is a model generated to estimate noise included in perspiration data. In other words, the noise model 41 is a model indicating a relationship between noise included in perspiration data, and the perspiration data and/or sensor data. During the correction process, the correction section 211 may acquire the noise model 41 stored in the server 40, and execute the correction process using the noise model 41.

The noise model 41 may be generated on the basis of sensor data acquired in advance. For example, such a noise model 41 may be generated as a model expressed by a function or the like that treats the noise value as the response variable, and singular or plural sensor data as parameters. By using the model, the values of other sensor data different from the perspiration data can be used to estimate noise included in the perspiration data. Therefore, the correction section 211 is able to remove estimated noise from perspiration data to correct the perspiration data.

For example, such a noise model 41 may be generated (or updated) by machine learning using perspiration data, sensor data acquired at the same time as the perspiration data, and output results of the process (for example, the presence or absence of noise, and whether the result of estimating the activity in the sympathetic nerves is correct or incorrect). As such machine learning, a publicly known algorithm such as deep learning or a variety of neural networks may be used, for example. By learning noise patterns, the noise specification accuracy and removal accuracy can be improved. Such a noise model 41 may be generated appropriately according to the number, combination, and the like of sensors usable at the same time as the perspiration sensor 11. In addition, such a noise model 41 may be selected appropriately according to the type or the like of a sensor that executes measurement at the same time as the perspiration sensor during the process by the processing section 210.

By applying sensor data measured by another sensor at the same time as the perspiration sensor 11 to the noise model 41, the correction section 211 is able to specify and also remove noise included in the perspiration data acquired by the perspiration sensor 11.

Also, although described in detail later, the noise model 41 used in the correction process by the correction section 211 may be updated as appropriate. For example, in the case in which the result of estimating the activity in the sympathetic nerves obtained after the correction process is accepted as being correct or incorrect, it is possible to make the feedback be reflected in the noise model 41. With this arrangement, the accuracy of the noise model 41 is improved, and the accuracy of the results of subsequent estimations of the activity in the sympathetic nerves is also improved.

Also, such a noise model 41 may be generated or updated in correspondence with the user on whom the information processing apparatus 10 is worn or attached. In other words, the noise model 41 may be associated with the user on whom the information processing apparatus 10 is worn or attached. The noise model 41 associated with the user is optimized for the user according to properties related to the state, body motion, and the like of the user. By using such a noise model 41 optimized for a specific user, the accuracy of the process of correcting perspiration data acquired from the user by the perspiration sensor 11 can be improved further.

Also, although described in detail later, by constructing a noise model 41 associated with a single user, the noise model 41 can be shared through the server 40 between information processing apparatus 10 realized in different modes. With this arrangement, even in the case in which the mode of the information processing apparatus 10 used by the user is different, by adopting a shared noise model 41, high accuracy of the process of correcting perspiration data related to the user can be maintained.

Also, in the initial stages, such a noise model 41 may also be a noise model 41 used in common with respect to multiple users. In other words, the noise model 41 may also be provided as a universal model generated by the machine learning of large amounts of perspiration data and sensor data in advance. With this arrangement, the accuracy of the result of estimating the activity in the sympathetic nerves of a user who uses the information processing apparatus 10 for the first time can be ensured. Also, through ongoing use and feedback for every user, such a universal noise model 41 may be updated appropriately as a noise model specialized for every user.

Note that the noise model 41 described above may be used to specify noise from only perspiration data acquired by the perspiration sensor 11, and to remove the noise. For example, as the noise model 41, a model that associates singular or plural sensor data and noise values at the time of model generation, and also associates the noise values with the perspiration data itself, may be generated. With this arrangement, for example, it becomes possible to estimate noise from the time-series change of perspiration data. Consequently, even in the case in which only the perspiration sensor 11 is provided in the information processing apparatus 10, the correction section 211 is able to execute the perspiration data correction process with high accuracy.

The above describes a correction process related to the removal of noise from perspiration data by the correction section 211 using the noise model 41. Note that the correction section 211 may also remove noise from perspiration data without using a noise model 41 like the above-described. For example, noise may also be removed from perspiration data by directly using sensor data acquired by a sensor that executes measurement at the same time as the perspiration sensor. More specifically, in the case in which the sensor data obtained from the other sensor changes to exceed a predetermined standard, the correction section 211 may execute a process of removing noise from perspiration data according to the degree of the change. By such a process, the accuracy of the perspiration data can be improved, even in cases in which the noise model 41 has not been constructed, or the learning of the noise model 41 is insufficient.

Note that the correction section 211 may also execute the correction process using context information acquired from the context acquisition section 220. A process using context information will be described later.

Figure 7:
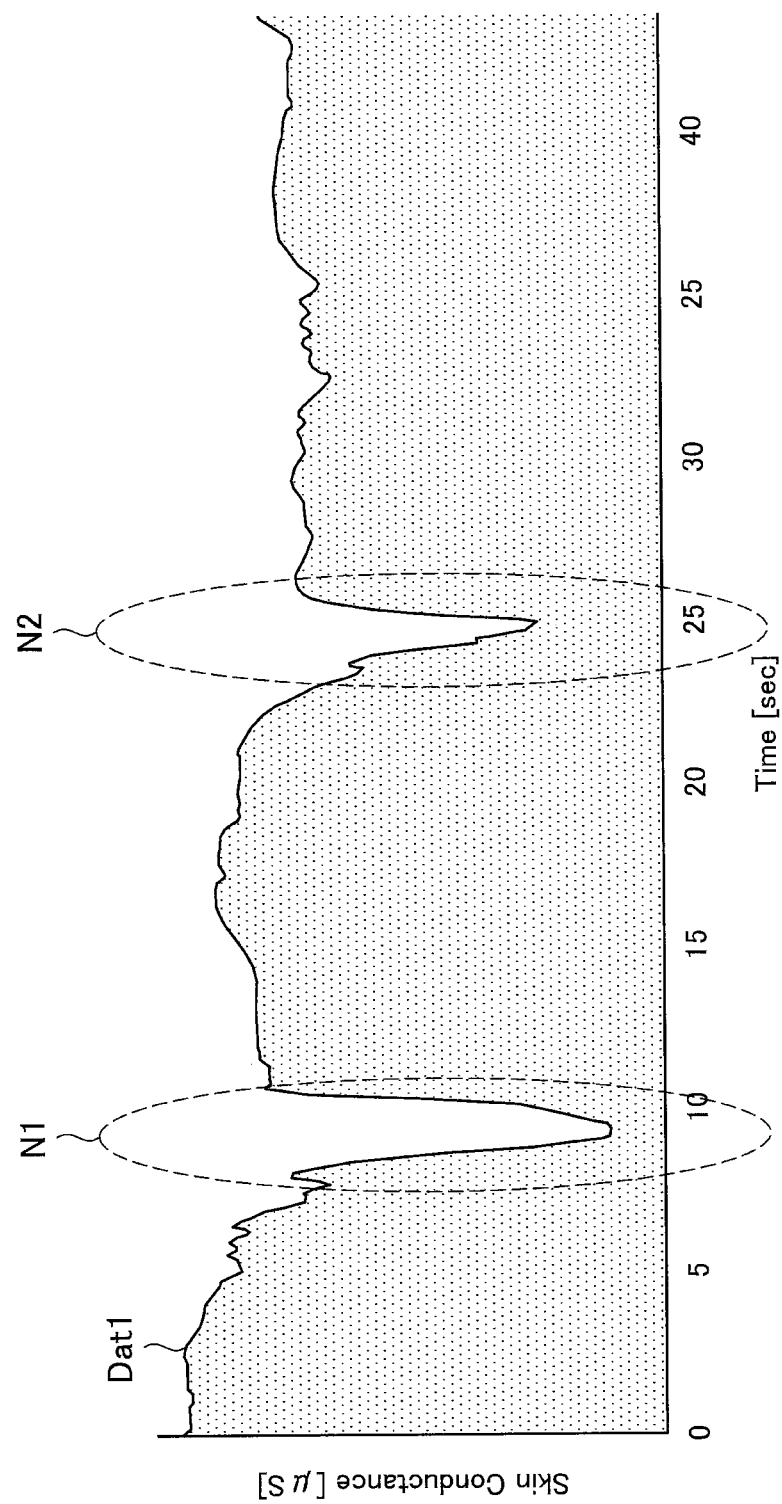
[FIG. 7]
Figure 8:
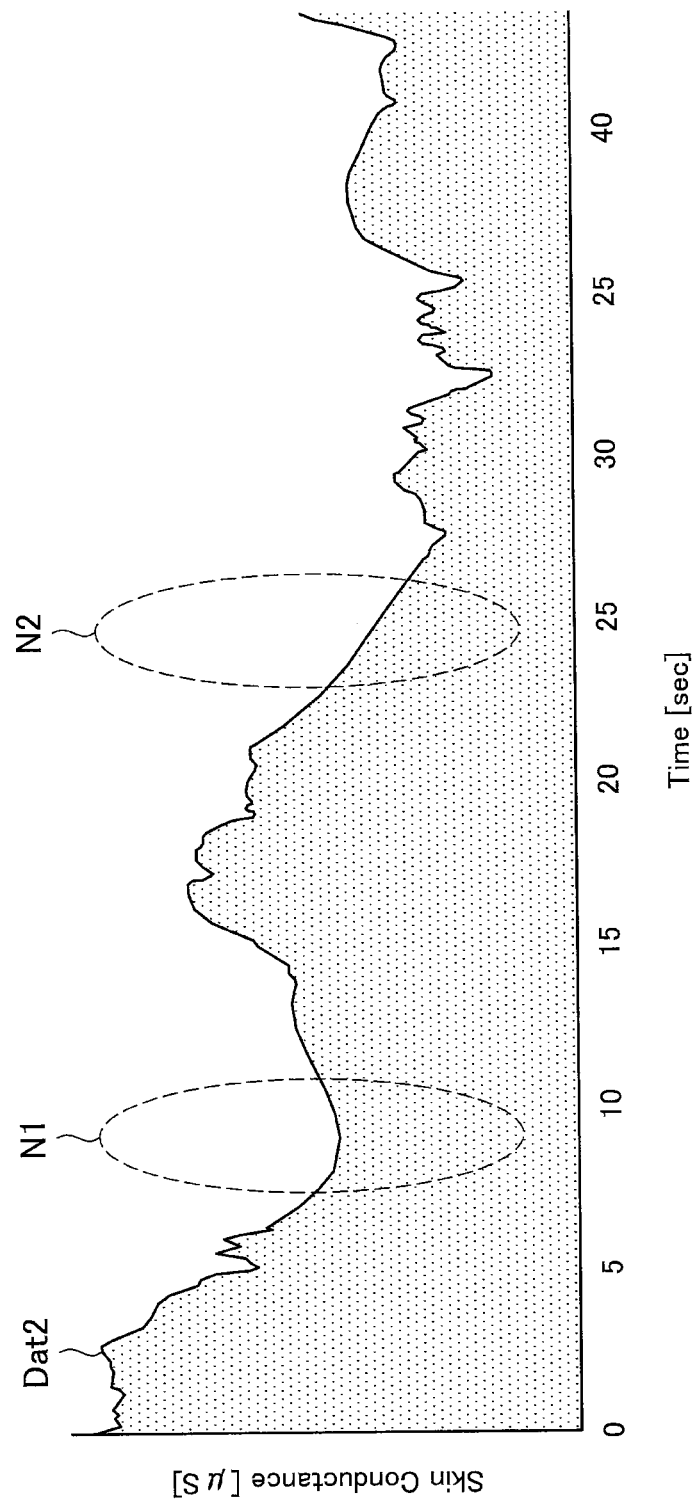
[FIG. 8]

Next, an example of a result of the correction process by the correction section 211 will be described. FIGS. 7 and 8 are graphs illustrating uncorrected and corrected perspiration data. The graph Dat1 illustrated in FIG. 7 is a graph illustrating time-series change of perspiration data before correction. Note that in this correction process, the noise model 41 is used.

As illustrated in FIG. 7, the graph Dat1 illustrates that in two time periods (the time periods illustrating the areas near the minimum values of the graph, enclosed by a dashed line N1 and a dashed line N2), the perspiration data changes suddenly. Herein, as illustrated by the graph in FIG. 6, it is thought that the perspiration sensor has become estranged from the skin by some kind of disturbance, and the perspiration data has not been measured correctly. Additionally, there is the possibility that noise is also included in the perspiration data measured outside these times due to influence caused by a disturbance.

On the other hand, the graph Dat2 illustrated in FIG. 8 is a graph illustrating the time-series change of perspiration data after the correction process has been performed by the correction section 211. First, the sudden changes in the perspiration data that were illustrated at the times N1 and N2 have been removed. Also demonstrated is that even in the other portions, characteristic changes in the perspiration data (such as quivering oscillations, for example) have been made distinct by the correction.

The above describes the correction process by the correction section 221. The correction section 211 outputs corrected perspiration data to the extraction section 212.

(Extraction Section)

The extraction section 212 includes a function of extracting mental perspiration data caused by mental perspiration from the corrected perspiration data. Specifically, on the basis of a predetermined algorithm, the extraction section 212 discriminates between mental perspiration data and thermal perspiration data in the corrected perspiration data, and extracts each kind of data.

As the predetermined algorithm above, for example, the method of measuring phasic activity (corresponding to mental perspiration) disclosed in Non-Patent Literature 1 above can be used. In this case, the extraction section 212 computes tonic activity (corresponding to thermal perspiration) and phasic activity on the basis of time-series data obtained by executing deconvolution operations on the corrected perspiration data. With this arrangement, the corrected perspiration data is extracted into mental perspiration data and thermal perspiration data.

Figure 9:
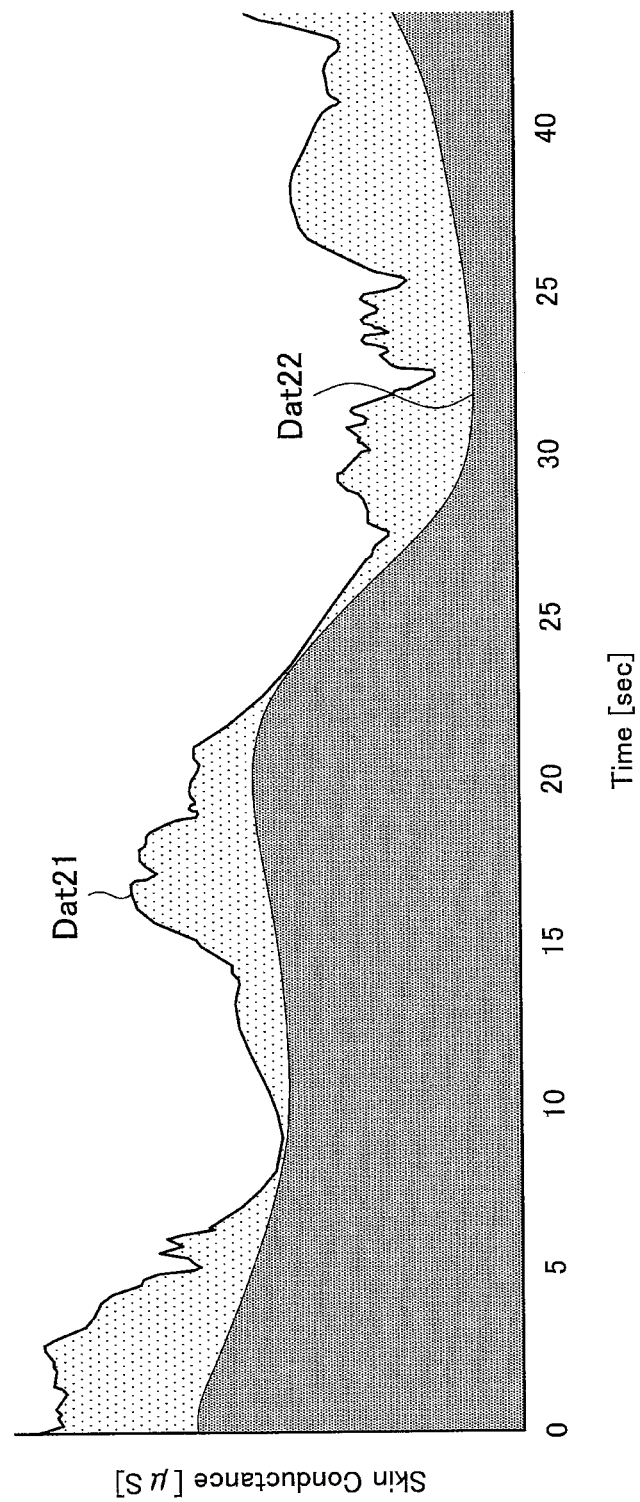
[FIG. 9]

FIG. 9 is a graph illustrating an example of an extraction result of mental perspiration data and thermal perspiration data extracted by the extraction section 212 according to the present embodiment. The region Dat21 corresponds to mental perspiration data, while the region Dat22 corresponds to thermal perspiration data. Whereas the time-series change of the thermal perspiration data related to the region Dat22 is sluggish, the time-series change of the mental perspiration data related to the region Dat21 is agile. This is because the latency associated with mental perspiration is shorter than the latency associated with thermal perspiration. By using the predetermined algorithm, the extraction section 212 extracts each of mental perspiration data and thermal perspiration data like the data illustrated in FIG. 9 from perspiration data.

Note that in the extraction process, the extraction section 212 may also use sensor data acquired by a different type of sensor than the perspiration sensor 11. For example, thermal perspiration may occur in accordance with the body temperature of the user on whom the information processing apparatus 10 is worn or attached. Also, since mental perspiration changes according to the state of tension of the user, the physiological phenomena of effectors that change according to the state of tension can be reflected in the extraction process.

Consequently, for example, the extraction section 212 may use data related to the body temperature, pulse wave, or blood pressure of the user acquired by the biological sensor 12, or the air temperature or humidity of the predetermined space acquired by the environmental sensor 30, as weights related to the above predetermined algorithm. Note that the weights related to the algorithm are one example of parameters used in the extraction process. With this arrangement, the accuracy of computing phasic activity and tonic activity may be improved. The above sensor data may be acquired by each sensor at the same time as the acquisition of perspiration data by the perspiration sensor 11.

In addition, the extraction section 212 may also execute the process of extracting mental perspiration data using an extraction model 42. Herein, the extraction model 42 is a model generated to extract mental perspiration data from perspiration data. In other words, the extraction model 42 is a model indicating a relationship between the parameters used in the extraction process above, and the corrected perspiration data and/or sensor data. For example, the extraction section 212 may execute a process of extracting mental perspiration data by applying sensor data acquired by the other sensor described above to the extraction model 42. Additionally, in the case of not acquiring sensor data from the other sensor, the extraction section 212 may also execute the extraction process using only the corrected perspiration data and the extraction model 42.

For example, such an extraction model 42 may be generated as a model expressed by a function or the like that treats the weights to apply to the predetermined algorithm above as response variables, and singular or plural sensor data as parameters. By using the model, the accuracy of the mental perspiration data extraction process can be improved. In this case, during the extraction process, the extraction section 212 may acquire the extraction model 42 stored in the server 40.

Such an extraction model 42 may be generated or updated in correspondence with the user on whom the information processing apparatus 10 is worn or attached. In other words, the extraction model 42 may be associated with the user on whom the information processing apparatus 10 is worn or attached. The extraction model 42 associated with the user is optimized for the user according to properties related to the state of the user, the environment where the user uses the information processing apparatus 10, and the like. For example, the perspiration amount or perspiration timing for mental perspiration and thermal perspiration is different depending on the predispositions of the user, such as excessive sweating or stage fright. Accordingly, the extraction model 42 may also include parameters and the like corresponding to every user, and in addition, the extraction model 42 may be updated appropriately with parameters suited to every user. By using such an extraction model 42 optimized for a specific user, the accuracy of the process of extracting mental perspiration data from perspiration data corrected according to the user can be improved further.

Also, in the initial stages, such an extraction model 42 may also be an extraction model 42 used in common with respect to multiple users. In other words, the extraction model 42 may also be provided as a universal model generated by the machine learning of large amounts of perspiration data and sensor data in advance. With this arrangement, the accuracy of the result of estimating the activity in the sympathetic nerves of a user who uses the information processing apparatus 10 for the first time can be ensured. Also, through ongoing use and feedback for every user, such a universal extraction model 42 may be updated appropriately as an extraction model specialized for every user.

Note that the extraction section 212 may also execute the above extraction process using context information acquired from the context acquisition section 220. A process using context information will be described later.

The extraction section 212 outputs extracted mental perspiration data (and thermal perspiration data) to the estimation section 213.

(Estimation Section)

The estimation section 213 includes a function of estimating the activity in the sympathetic nerves of the user corresponding to the perspiration data on the basis of extracted mental perspiration data. Specifically, the estimation section 213 uses mental perspiration data to estimate the activity in the sympathetic nerves of the user corresponding to the perspiration data. As described above, generally, mental perspiration is linked to activity in the sympathetic nerves, but is not linked to activity in the parasympathetic nerves. For this reason, the estimation section 213 estimating the activity in the sympathetic nerves on the basis of mental perspiration data substantially corresponds to estimating the activity in the autonomic nerves. Consequently, for example, the estimation section 213 is also able to estimate the activity in the parasympathetic nerves indirectly from the activity in the sympathetic nerves estimated on the basis of mental perspiration data.

For example, the estimation section 213 may estimate the activity in the sympathetic nerves of the user on the basis of a time-series distribution of mental perspiration data. For example, the estimation section 213 may estimate the activity in the sympathetic nerves of the user on the basis of the number of peaks and the peak strength in the mental perspiration data, the value of the integral (area value) of a graph related to the distribution, or the magnitude of change in the data within a predetermined time. These may be set appropriately as parameters related to the estimation process. Additionally, the estimation section 213 may also estimate the activity in the sympathetic nerves of the user on the basis of a frequency spectrum or the like obtained by performing frequency analysis of the mental perspiration data. For example, the estimation section 213 may also estimate the activity in the sympathetic nerves of the user on the basis of the relative sizes of the peak frequencies in the frequency spectrum.

Figures 10A, 10B:
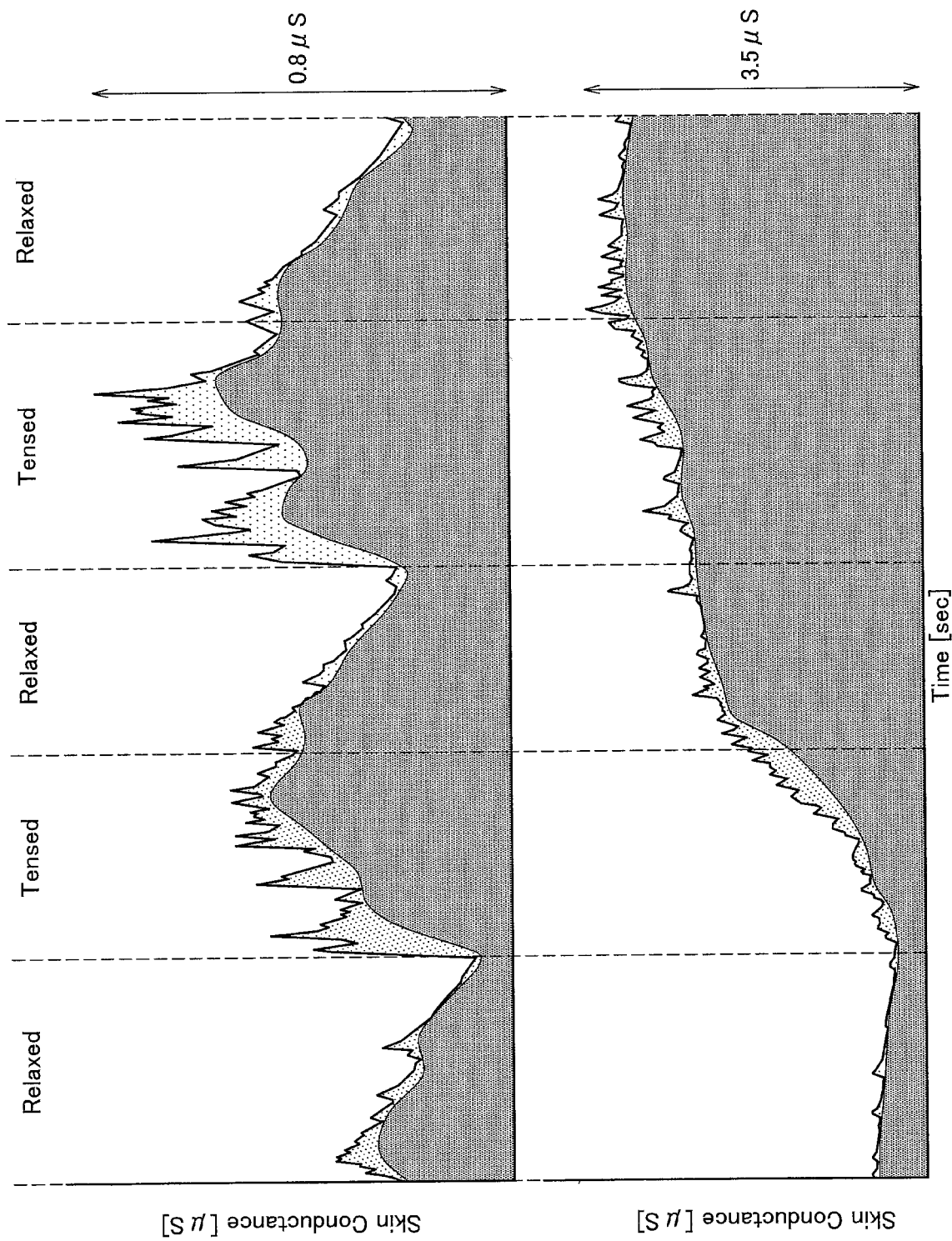
[FIGS. 10A and 10B]

FIGS. 10A and 10B are diagrams for explaining an example of a sympathetic nerve estimation method based a time-series distribution of mental perspiration data. FIG. 10A is a graph illustrating time-series distributions of mental perspiration data and thermal perspiration data obtained by an information processing apparatus 10 worn on a finger of the hand, while FIG. 10B is a graph illustrating time- series distributions of mental perspiration data and thermal perspiration data obtained by an information processing apparatus 10 worn on the wrist. Each of the segments labeled "Relaxed" and "Tensed" illustrated in FIGS. 10A and 10B is a time period during which the person being measured is relaxing and a time period during which the person being measured is performing work that imposes a psychological load, respectively. For this reason, it is thought that in the segments associated with "Relaxed", the activity in the parasympathetic nerves is dominant, whereas in the segments associated with "Tensed", the activity in the sympathetic nerves is dominant.

Referring to FIGS. 10A and 10B, it is demonstrated that in the segments associated with "Tensed", the number of peaks and the peak strength in the mental perspiration data, the value of the integral of the graph related to the distribution, and the change in the data are greater than the segments associated with "Relaxed". Consequently, from the time-series distribution of the mental perspiration data, it is possible to estimate the activity in the sympathetic nerves.

For example, in the case in which the number of peaks and the peak strength in the mental perspiration data or an indicator related to the change in the data within a predetermined time exceeds a predetermined threshold value, the estimation section 213 may estimate that the activity in the sympathetic nerves is dominant Additionally, the estimation section 213 may also estimate an evaluation value related to the dominance of the activity in the sympathetic nerves according to the number of peaks and the peak strength in the mental perspiration data or the magnitude of the indicator related to the change in the data within a predetermined time. With this arrangement, the degree of activity in the sympathetic nerves can be estimated quantitatively. In other words, more detailed analysis or processing using the estimation result becomes possible.

Note that, referring to FIG. 10A, it is observed that in the segments associated with "Tensed", the EDA value of thermal perspiration rises, while in the segments associated with "Relaxed", the EDA value of thermal perspiration falls. From the above, the estimation section 213 can also estimate the activity of the sympathetic nerves on the basis of extracted thermal perspiration data. Note that in FIG. 10B, changes in the thermal perspiration data corresponding to changes in the state of the person being measured do not appear distinctly. This is because the amount of perspiration related to thermal perspiration is greater at the wrists than at the fingers of the hands.

Note that in the estimation process, the estimation section 213 may also use sensor data acquired by a different type of sensor than the perspiration sensor 11. For example, as described above, the physiological phenomena of effectors are related to activity in the sympathetic nerves and the parasympathetic nerves. For this reason, the estimation section 213 may also estimate the activity in the sympathetic nerves by taking into account sensor data related to the state of the user acquired from the biological sensor 12, the tracking sensor 13, or the environmental sensor 30. With this arrangement, the estimation accuracy can be improved. The above sensor data may be acquired by each sensor at the same time as the acquisition of perspiration data by the perspiration sensor 11.

In addition, the estimation section 213 may also execute the process of estimating the activity in the sympathetic nerves using the activity estimation model 43. The activity estimation model 43 is a model generated to estimate the activity in the sympathetic nerves. In other words, the activity estimation model 43 is a model indicating a relationship between the parameters used in the estimation process above, and the mental perspiration data and/or sensor data. For example, the estimation section 213 may execute a process of estimating the activity in the sympathetic nerves by applying sensor data acquired by the other sensor described above to the activity estimation model 43. Additionally, in the case of not acquiring sensor data from the other sensor, the estimation section 213 may also execute the estimation process using only the mental perspiration data and the activity estimation model 43.

For example, such an activity estimation model 43 may be generated as a model expressed by a function or the like that treats the parameters related to the estimation process above as response variables, and singular or plural sensor data as parameters. By using the model, the accuracy of the process of estimating the activity in the sympathetic nerves can be improved. In this case, during the estimation process, the estimation section 213 may acquire the activity estimation model 43 stored in the server 40.

Such an activity estimation model 43 may be generated or updated in correspondence with the user on whom the information processing apparatus 10 is worn or attached. In other words, the activity estimation model 43 may be associated with the user on whom the information processing apparatus 10 is worn or attached. The activity estimation model 43 associated with the user is optimized for the user according to properties related to the state of the user, the environment where the user uses the information processing apparatus 10, and the like. For example, as described above, the perspiration amount or perspiration timing for mental perspiration and thermal perspiration is different depending on the predispositions of the user, such as excessive sweating or stage fright. In other words, the number of peaks and the peak strength in the mental perspiration data, an indicator related to the change in the data, and the like is different in degree depending on the user. Accordingly, the activity estimation model 43 may also include threshold values related to the estimation of the activity in the sympathetic nerves corresponding to every user, and in addition, the activity estimation model 43 may be updated appropriately with threshold values suited to every user. By using such an activity estimation model 43 optimized for a specific user, the accuracy of estimating the activity in the sympathetic nerves of the user can be improved further.

Also, in the initial stages, such an activity estimation model 43 may also be an activity estimation model 43 used in common with respect to multiple users. In other words, the activity estimation model 43 may also be provided as a universal model generated by the machine learning of large amounts of perspiration data and sensor data in advance. With this arrangement, the accuracy of the result of estimating the activity in the sympathetic nerves of a user who uses the information processing apparatus 10 for the first time can be ensured. Also, through ongoing use and feedback for every user, such a universal activity estimation model 43 may be updated appropriately as an activity estimation model specialized for every user.

Note that the estimation section 213 may also execute the above estimation process using context information acquired from the context acquisition section 220. A process using context information will be described later.

The estimation section 213 outputs the estimation result for the activity in the sympathetic nerves to the output control section 230. Additionally, the estimation section 213 may also output the estimation result to the feedback section 240.

(Context Acquisition Section)

The context acquisition section 220 includes a function of acquiring context information related to the user on whom the perspiration sensor 11 is worn or attached. The context acquisition section 220 according to the present embodiment acquires context information related to the user on whom the information processing apparatus 10 is worn or attached. The processing section 210 may also execute each process using context information acquired by the context acquisition section 220. For example, the correction section 211 may execute the correction process using the context information. Also, the extraction section 212 may execute the extraction process using the context information. Also, the estimation section 213 may execute the estimation process using the context information.

Herein, context information refers to information indicating the activity conditions of the user or the environment around the user. For example, the context information may include information related to the user's posture (such as a standing, sitting, or supine position), behavior (such as being still, working, studying, exercising, chatting, eating, operating machinery, or driving), and action history (such as means of transportation, times, purposes of action, text information or tag information posed on a social networking service (SNS) or the like, or a schedule). In addition, the context information may also include information related to categories (indoor, outdoor) of the environment around the user, the geographical region, the season, the air temperature, the humidity, the running conditions of home appliances (for example, air-conditioning equipment such as an air conditioner), and the like.

This context information is related to the physiological phenomena of effectors. For this reason, by using context information in each process executed by the processing section 210 described above, the processing accuracy can be raised further. For example, depending on the measurement site of the perspiration sensor 11, such as the wrist, sites where large amounts of perspiration related to thermal perspiration occur also exist. By applying context information about the perspiration data related to such sites to each process, it becomes possible to improve the accuracy of removing noise from the perspiration data, accurately extract mental perspiration data, and accurately estimate the activity in the sympathetic nerves.

(Output Control Section)

The output control section 230 controls output regarding the result of estimating the activity in the sympathetic nerves acquired from the processing section 210 (estimation section 213). The output referred to herein is not limited to simply outputting an estimation result processed and obtained by the processing section 210 to the outside of the control section 20. For example, the output control section 230 may also control output according to the estimation result.

Output according to the estimation result is output given in any mode to the user on whom the information processing apparatus 10 is worn or attached. This output is not limited to the simple presentation of a numerical value, graph, or the like that indicates the result of estimating the activity in the sympathetic nerves. For example, the output may also be information that is useful to the user, or alternatively, information or a stimulus that promotes user wakefulness. Useful information may refer to a suggestion, advice, or the like to the user, for example. More specifically, for example, the output may be a suggestion for the user to take a break, advice informing the user that one's concentration is high, or the like. In addition, for example, the information or stimulus that promotes user wakefulness may be sound such as an alarm, a warning, or the like, an image or the turning on or blinking of a light-emitting device, a physical stimulus (such as vibration or an electrical stimulus), or the like. By such output, it becomes possible to provide information or a stimulus to the user suitably.

Such output may be executed by the input/output device 14, for example. In this case, the output control section 230 outputs information related to the output to the input/output device 14. Also, the presentation may be executed by any output device provided externally to the information processing apparatus 10. In this case, the output control section 230 may also output information related to the output to the output device through the communication section 21, the network NW, and the like.

Note that a specific example of the control of the output by the output control section 230 will be described later.

(Feedback Section)

The feedback section 240 acquires feedback-related information about the estimation result obtained by the processing section 210, and updates various models on the basis of the feedback-related information. For example, the feedback section 240 may update at least one of the noise model 41, the extraction model 42, and the activity estimation model 43 on the basis of the feedback-related information.

For example, the feedback section 240 may acquire information input by the user into the input/output device 14 as the feedback-related information. The information input by the user corresponds to a user response with respect to the estimation result for the activity in the sympathetic nerves. In other words, the user inputs a response related to whether the estimation is correct or incorrect into the input/output device 14 as the feedback-related information, and the feedback section 240 acquires this response as the feedback-related information. The response related to whether the estimation result is correct or incorrect may also be a numerical value or the like indicating the degree to which the estimation result is correct.

Note that the feedback-related information described above is not limited to information input by the user. For example, the feedback-related information may also be information based on the degree, degree of divergence, difference, or the like between the activity in the sympathetic nerves estimated from the perspiration data and the activity in the sympathetic nerves estimated from sensor data acquired by another sensor. In other words, the feedback-related information may be information which is not input by the user, but generated automatically on the basis of a comparison or the like with an estimation result based on other sensor data.

Next, the feedback section 240 updates at least one of the models on the basis of the acquired feedback-related information. For example, in the case of acquiring information responding that the estimation result is incorrect, the feedback section 240 infers the cause of the error, and updates the model related to the inferred cause. More specifically, in the case of inferring that the cause is in a process related to noise removal, the feedback section 240 may update the noise model 41. Similarly, in the case of inferring that the cause is in the mental perspiration data extraction process, the feedback section 240 may update the extraction model 42, and in the case of inferring that the cause is in the process of estimating the activity in the sympathetic nerves, the feedback section 240 may update the activity estimation model 43. Note that the process of updating each model by the feedback section 240 is realized by a publicly known algorithm, such as backpropagation or gradient methods in deep learning or neural networks, for example.

By such updating of each model by the feedback section 240, the accuracy of each of the processes using each of the updated models may be improved. Also, in the case in which each model is associated with a user, since models optimized for the user can be constructed, it becomes possible to obtain a suitable estimation result according to the user.

The above describes the configurations and functions of the information processing system 1 and the information processing apparatus 10 with reference to FIGS. 3, 4, 5, 6, 7, 8, 9, 10A and 10B.

Note that the functional configurations of the information processing system 1 and the information processing apparatus 10 illustrated in FIGS. 3 and 5 are merely one example of an embodiment of the present disclosure, and the present disclosure is not limited to such an example. For example, the device worn by the user may also be a sensing device including the functions of the perspiration sensor 11 and at least one of the biological sensor 12 and the tracking sensor 13. In this case, the control section 20, the communication section 21, and the storage section 22 may also be realized by one or multiple servers as the information processing apparatus. Also, in this case, the input/output device 14 may be provided as an independent configuration. In other words, as an embodiment, insofar as the information processing apparatus 10 acquires sensor data obtained from each sensor such as the perspiration sensor 11 worn on or attached to a user, and estimates the activity in the sympathetic nerves on the basis of the acquired data (that is, includes the functions of the processing section 210 according to the present embodiment), the specific mode of the information processing apparatus 10 is not particularly limited.

Also, each model stored in the server 40 may also be stored in the storage section 22. In other words, each model may also be provided inherently in the information processing apparatus 10.

<2.3. Process Flows>

Figure 11:
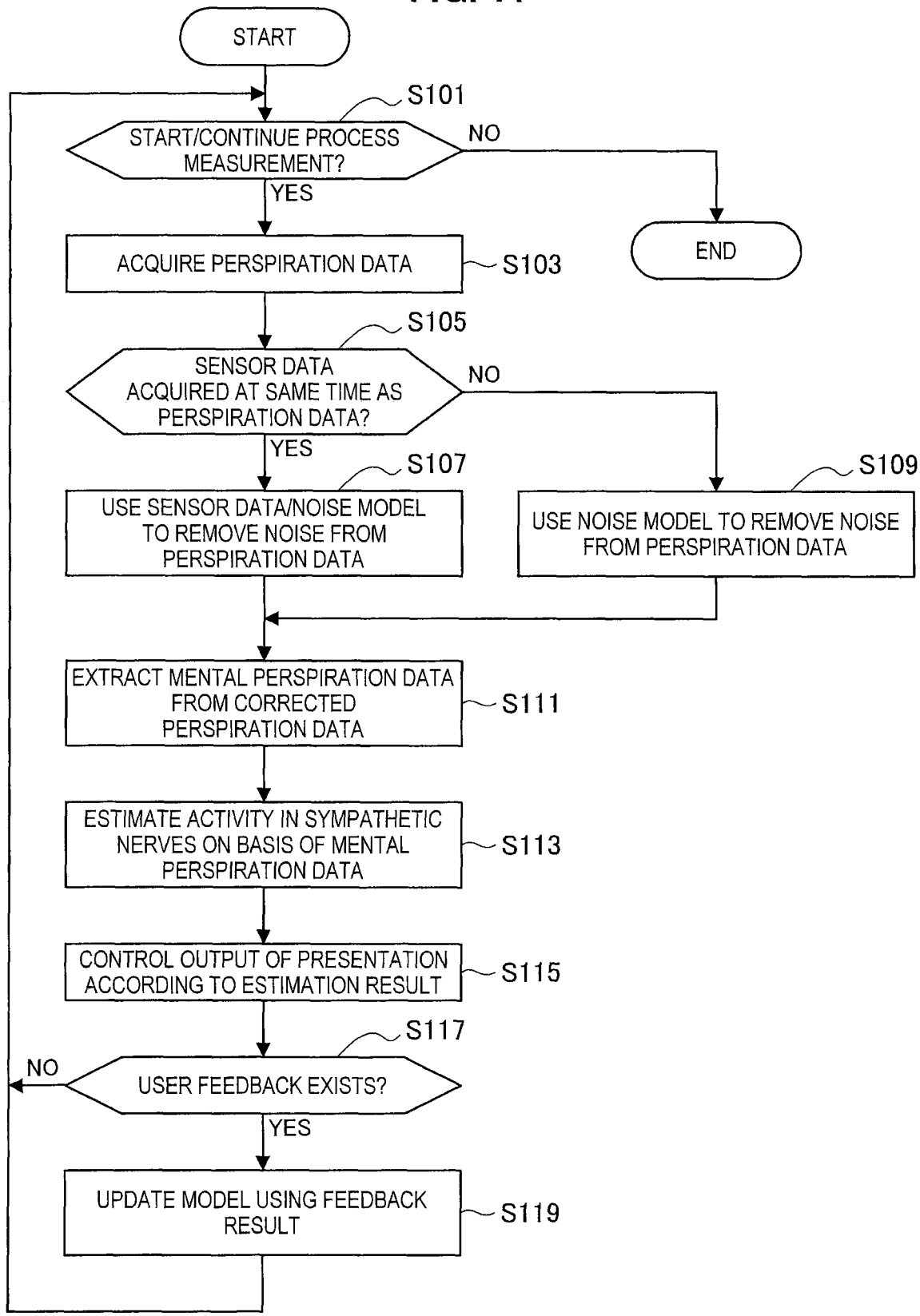
FIG. 11 is a flowchart illustrating an example of the flow of a process by the information processing apparatus according to the embodiment.

Next, FIG. 11 will be referenced to describe an example of the flow of a process by the information processing apparatus 10 according to the present embodiment. FIG. 11 is a flowchart illustrating an example of the flow of a process by the information processing apparatus 10 according to the present embodiment.

Referring to FIG. 11, the information processing apparatus 10 starts the process (step S101/YES), and first acquires perspiration data from the perspiration sensor 11 (step S103).

Next, the information processing apparatus 10 removes noise from the perspiration data obtained by the perspiration sensor 11, and executes a correction process that corrects the perspiration data (steps S105 to S109). For example, in the case in which the information processing apparatus 10 has acquired sensor data from another sensor at the same time as the perspiration data acquired by the perspiration sensor 11 (step S105/YES), the information processing apparatus 10 uses at least one of the sensor data acquired at the same time and the noise model 41 to remove noise included in the perspiration data (step S107). On the other hand, in the case in which the information processing apparatus 10 has not acquired sensor data from another sensor at the same time as the perspiration data acquired by the perspiration sensor 11 (step S105/NO), the information processing apparatus 10 uses the noise model 41 to remove noise included in the perspiration data (step S109). The correction process is executed by the correction section 211.

Next, the information processing apparatus 10 executes an extraction process of extracting at least mental perspiration data from the corrected perspiration data (step S111). The extraction process is executed by the extraction section 212.

Next, the information processing apparatus 10 executes an estimation process of estimating the activity in the sympathetic nerves on the basis of the extracted mental data (step S113). The estimation process is executed by the estimation section 213.

Next, the information processing apparatus 10 controls the output according to the estimation result (step S115). The control of the output is executed by the output control section 230. Also, the output is output by the input/output device 14.

Next, the information processing apparatus 10 receives feedback from the user (step S117). In the case in which feedback is input by the user (step S117/YES), the information processing apparatus 10 executes an update process related to the updating of each model using feedback-related information (step S119). The update process is executed by the feedback section 240.

The information processing apparatus 10 successively repeats the process associated with steps S103 to S119 described above until the process is ended (step S101/N0).

The above describes the information processing system 1 and the information processing apparatus 10 according to the present embodiment.

<<3. Applied Examples>>

Next, applied examples of the information processing system 1 according to the present embodiment will be described.

<3.1. Using to Improve Work Efficiency>

As described above, the information processing system 1 according to the present embodiment is able to estimate the activity in the sympathetic nerves. For example, the information processing system 1 may monitor the state of concentration (reflecting the activity in the sympathetic nerves) of the user who uses the system, and output to the user a presentation related to a suggestion or advice related to concentration. With this arrangement, the user can be encouraged to sustain and restore concentration. Consequently, for example, the efficiency related to work that requires concentration can be improved.

Figure 12:
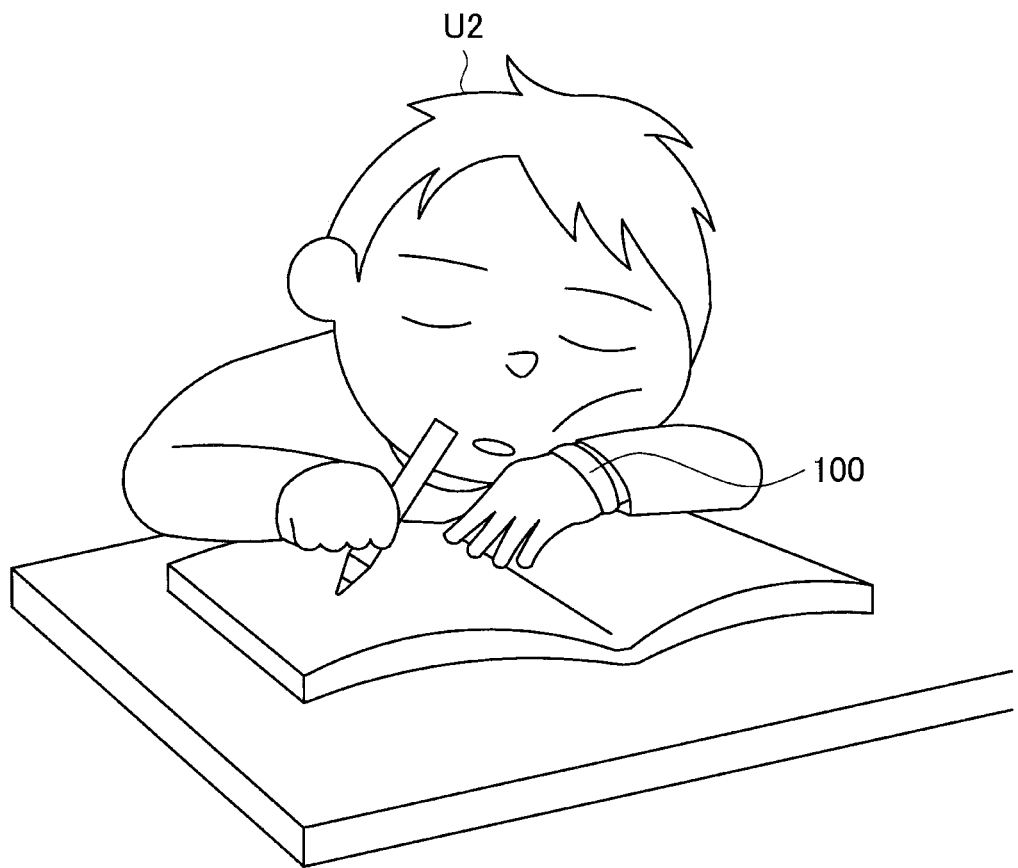
FIG. 12 is a diagram illustrating a first state of a user wearing the information processing apparatus in a first applied example.
Figure 13:
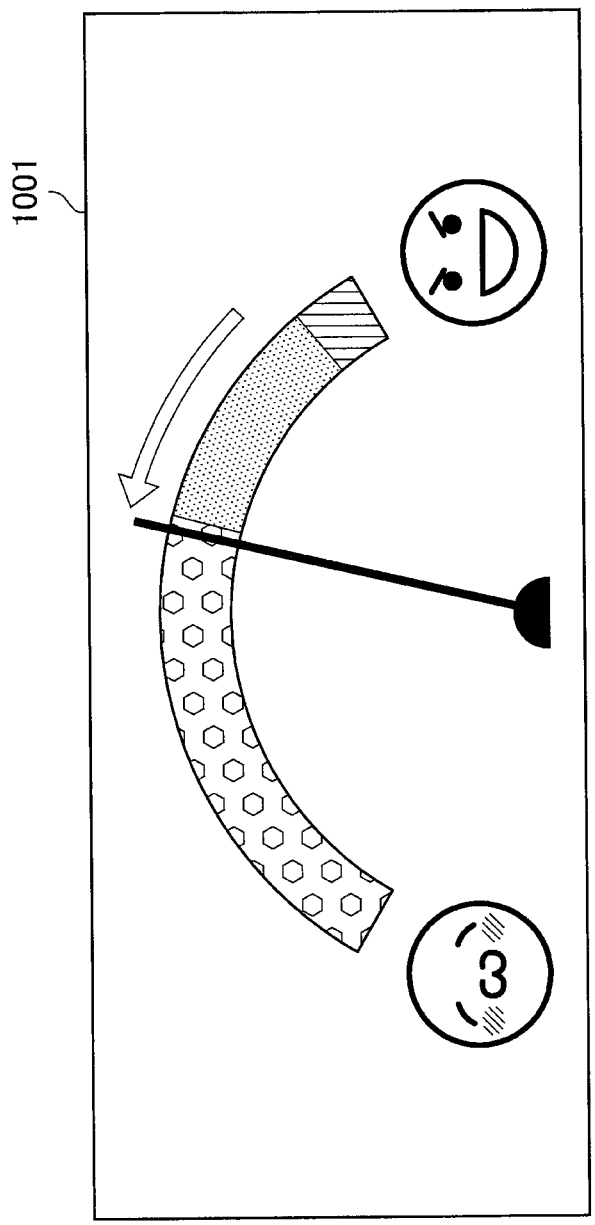
FIG. 13 is a diagram illustrating an example of a display utilizing an estimation result corresponding to the first state of the user.
Figure 14:
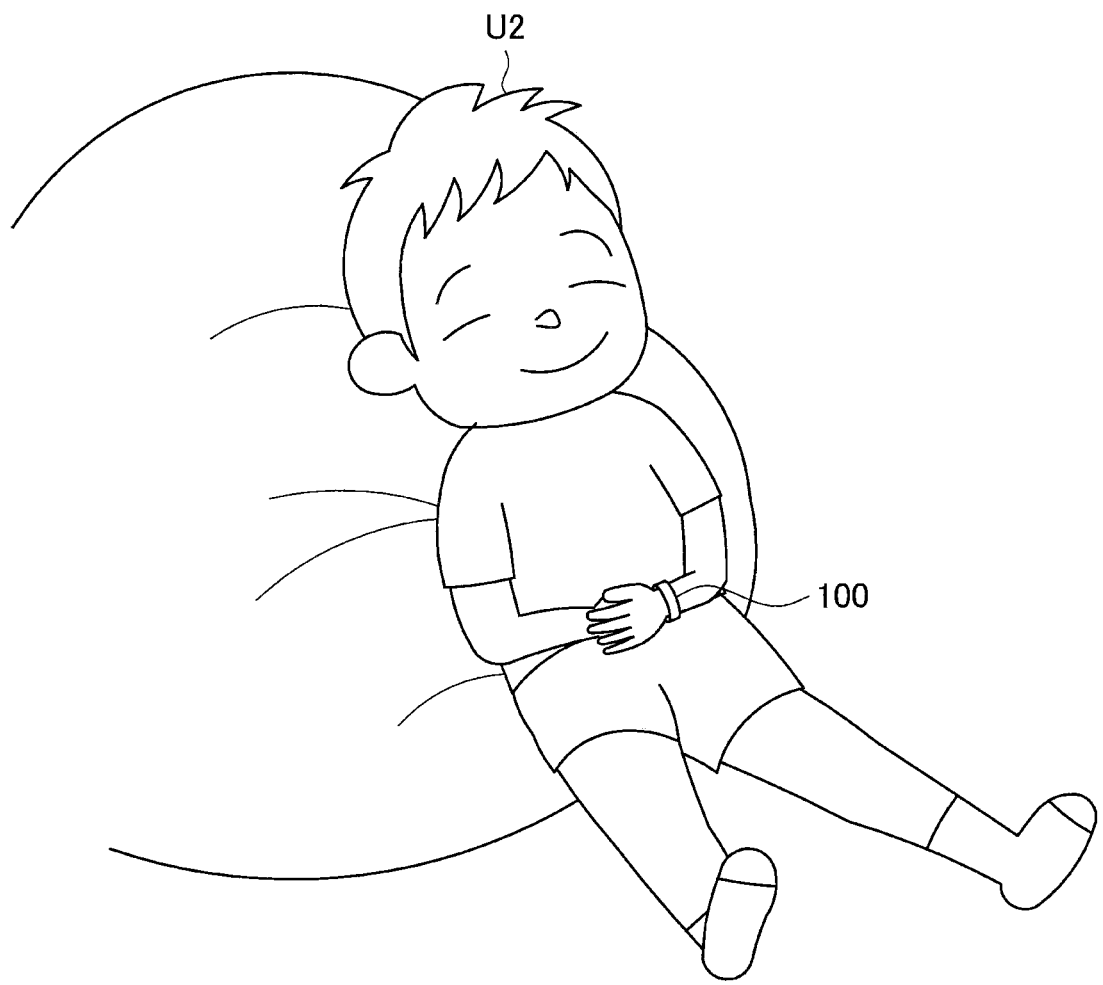
FIG. 14 is a diagram illustrating a second state of the user wearing the information processing apparatus in the first applied example.
Figure 15:
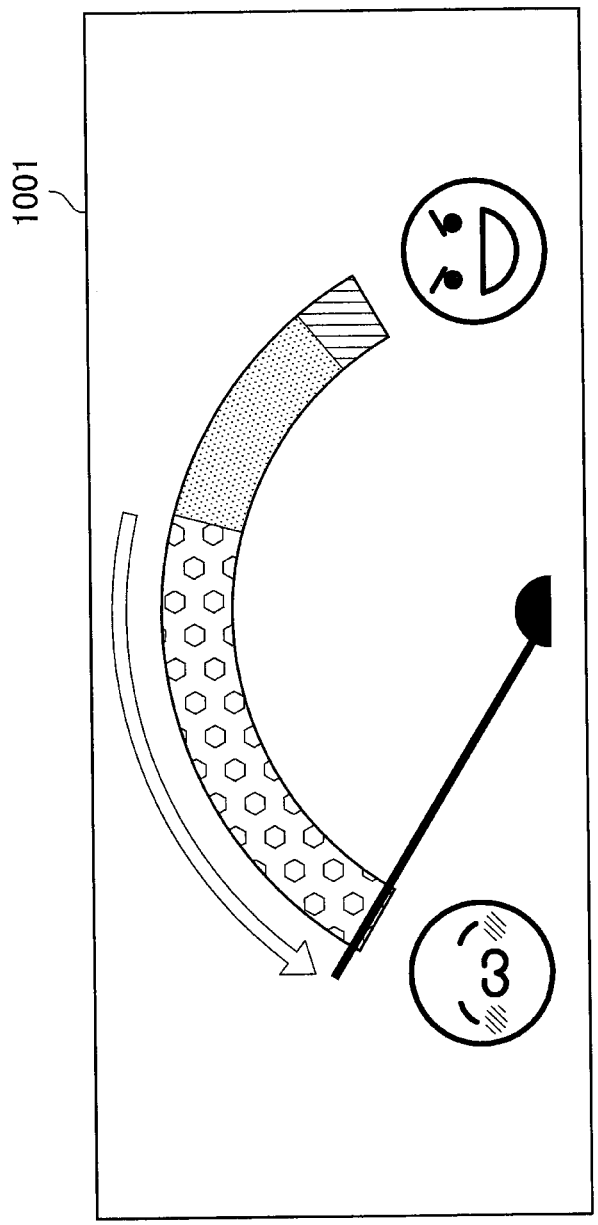
FIG. 15 is a diagram illustrating an example of a display utilizing an estimation result corresponding to the second state of the user.
Figure 16:
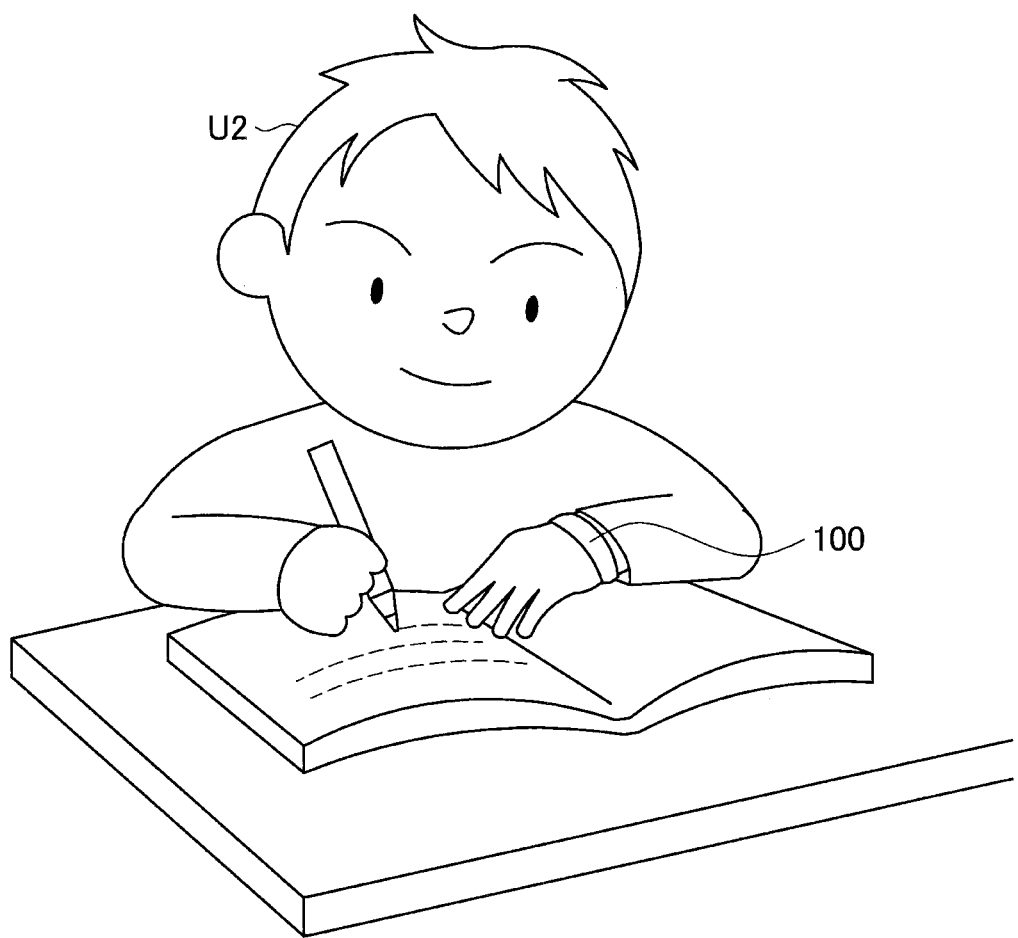
FIG. 16 is a diagram illustrating a third state of the user wearing the information processing apparatus in the first applied example.
Figure 17:
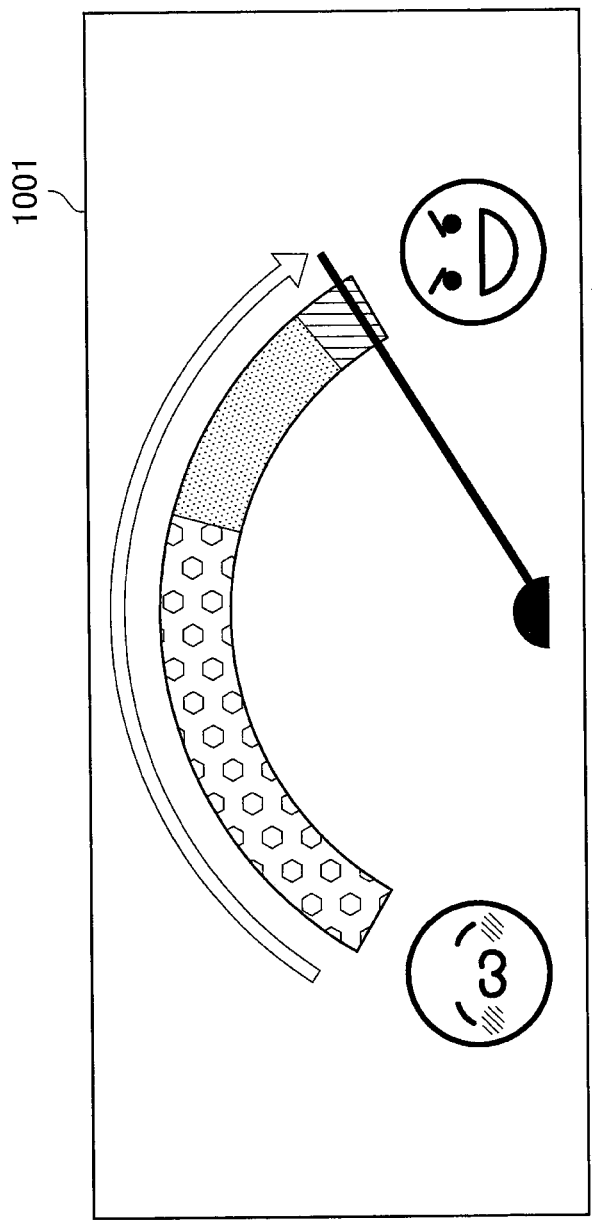
FIG. 17 is a diagram illustrating an example of a display utilizing an estimation result corresponding to the third state of the user.

FIGS. 12 to 17 are diagrams for explaining a first applied example of the information processing system 1 according to the present embodiment. FIG. 12 is a diagram illustrating a first state of a user wearing a wristwatch-style device 100, which is one mode of realizing the information processing apparatus 10. FIG. 13 is a diagram illustrating an example of a display utilizing an estimation result corresponding to the first state of the user. FIG. 14 is a diagram illustrating a second state of the user wearing the wristwatch-style device 100. FIG. 15 is a diagram illustrating an example of a display utilizing an estimation result corresponding to the second state of the user. FIG. 16 is a diagram illustrating a third state of the user wearing the wristwatch-style device 100. FIG. 17 is a diagram illustrating an example of a display utilizing an estimation result corresponding to the third state of the user.

Referring to FIG. 12, a user U2 who wears the wristwatch-style device 100 is studying, but has lost concentration, and thus is in a state (first state) of being slumped over a desk. In this case, the wristwatch-style device 100 executes the processes by the processing section 210 described above, and may estimate that the activity in the sympathetic nerves has fallen. Having done so, the wristwatch-style device 100 makes a presentation related to the falling of the activity. For example, as illustrated by the callout in FIG. 12, the wristwatch-style device 100 may output to the user U2 a presentation by speech that encourages activity in the parasympathetic nerves, such as "Let's take a break". Also, as illustrated in FIG. 13, the wristwatch-style device 100 may also output an indication that the user's concentration is falling to the user U2 by a display 1001 that indicates the state of the user's concentration. Note that in the meter illustrated in the display 1001, the position of the needle indicates the degree of the user's concentration. Specifically, the farther the needle is positioned on the right side, the more that concentration may be illustrated as being sustained, whereas the farther the needle is positioned on the left side, the more that concentration may be illustrated as being lapsed. Also, as illustrated in the display 1001, a bar that diagrammatically illustrates the activity in the sympathetic nerves corresponding to the position of the needle may be displayed as well. In FIG. 13, the needle may be illustrated as moving to the left due to lowered concentration.

Next, referring to FIG. 14, the user U2 who wears the wristwatch-style device 100 is resting (second state). In this case, the wristwatch-style device 100 may estimate that the activity in the sympathetic nerves has nearly stopped. Having done so, the wristwatch-style device 100 makes a presentation related to sufficient rest. For example, as illustrated by the callout in FIG. 14, the wristwatch-style device 100 may output to the user U2 a presentation by speech that encourages one to stop resting and resume work, such as "You have rested enough". Also, as illustrated in FIG. 15, the wristwatch-style device 100 may also output an indication that the user U2 is in a sufficiently relaxed state to the user U2 by the display 1001.

Next, referring to FIG. 16, the user U2 who wears the wristwatch-style device 100 has resumed studying (third state). In this case, the wristwatch-style device 100 may estimate that the activity in the sympathetic nerves is nearly dominant Having done so, the wristwatch-style device 100 makes a presentation related to the restoration of concentration by the resting. For example, as illustrated in FIG. 17, the wristwatch-style device 100 may present a state that the concentration of the user U2 has been restored completely to the user U2 by the display 1001. In this way, by estimating the activity in the sympathetic nerves of the user U2, and making a presentation related to sustaining and restoring concentration, it becomes possible to improve the work efficiency of the user U2.

The above describes the first applied example of the information processing system 1 according to the present embodiment. Note that the information processing system 1 is not limited to uses for improving work efficiency while studying or the like as illustrated in the present applied example For example, as illustrated in FIG. 1, the present technology may also be used to bring out a player's capabilities fully in a sport or tabletop game where concentration is demanded. Also, in the case in which the concentration of a user enjoying content with respect to the content has lapsed, the present technology may be used to encourage the user to discontinue the enjoyment of the content or switch to the enjoyment of other content. In other words, the information processing system 1 is applicable to all scenarios where sustaining or restoring user concentration is demanded.

<3.2. Detecting Sleepiness and Imparting Stimulus>

Also, the information processing system 1 according to the present embodiment may use an estimation result of the activity in the sympathetic nerves to detect sleepiness of a user who is a monitoring target of the information processing system 1. In addition, on the basis of the detection result, the information processing system 1 may also impart a stimulus to the user by an alarm or the like. With this arrangement, it becomes possible to wake a user who is in a sleeping state or a drowsy state.

Figure 18:
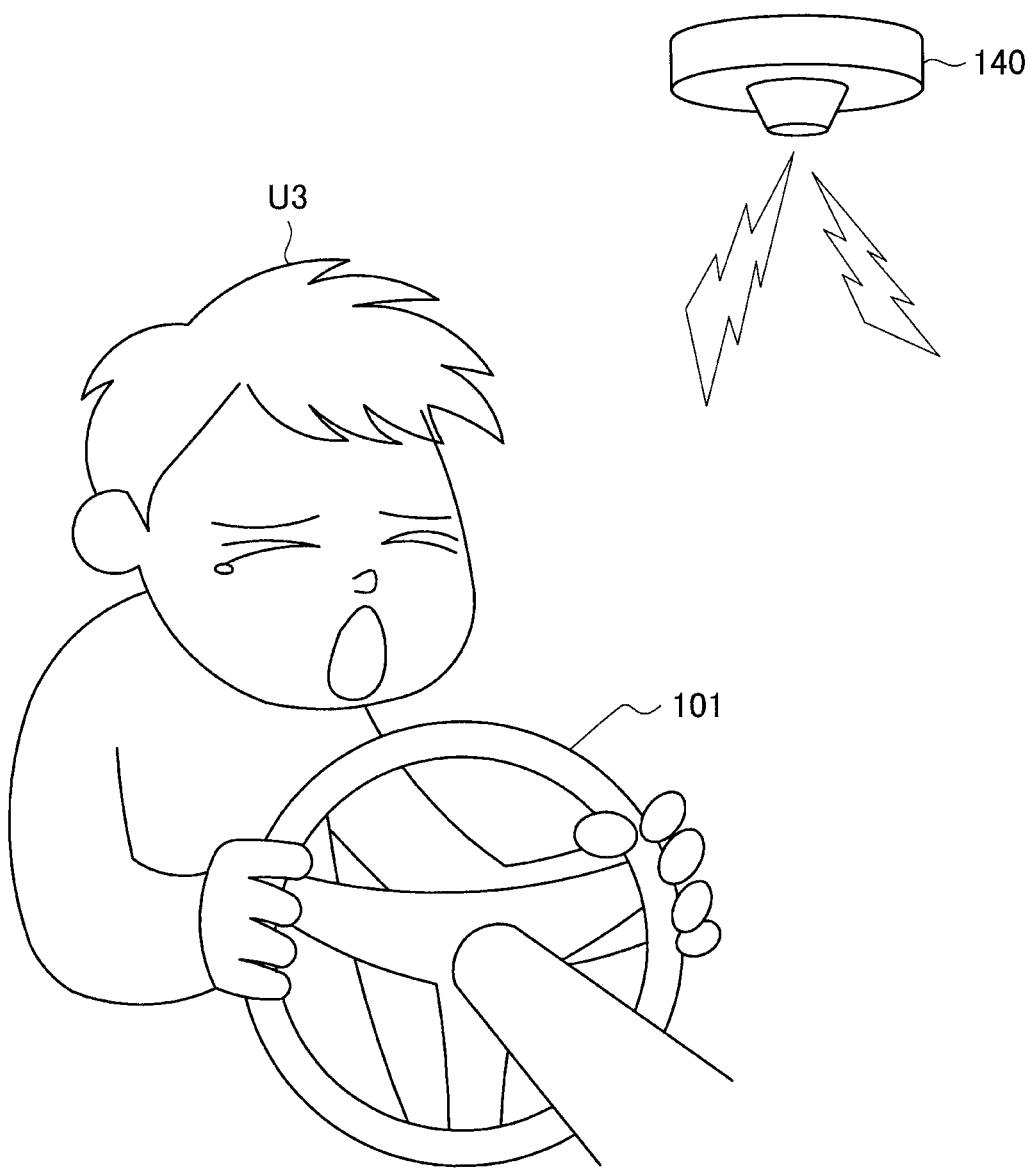
FIG. 18 is a diagram illustrating an example of an application situation of a second applied example.
Figure 19:
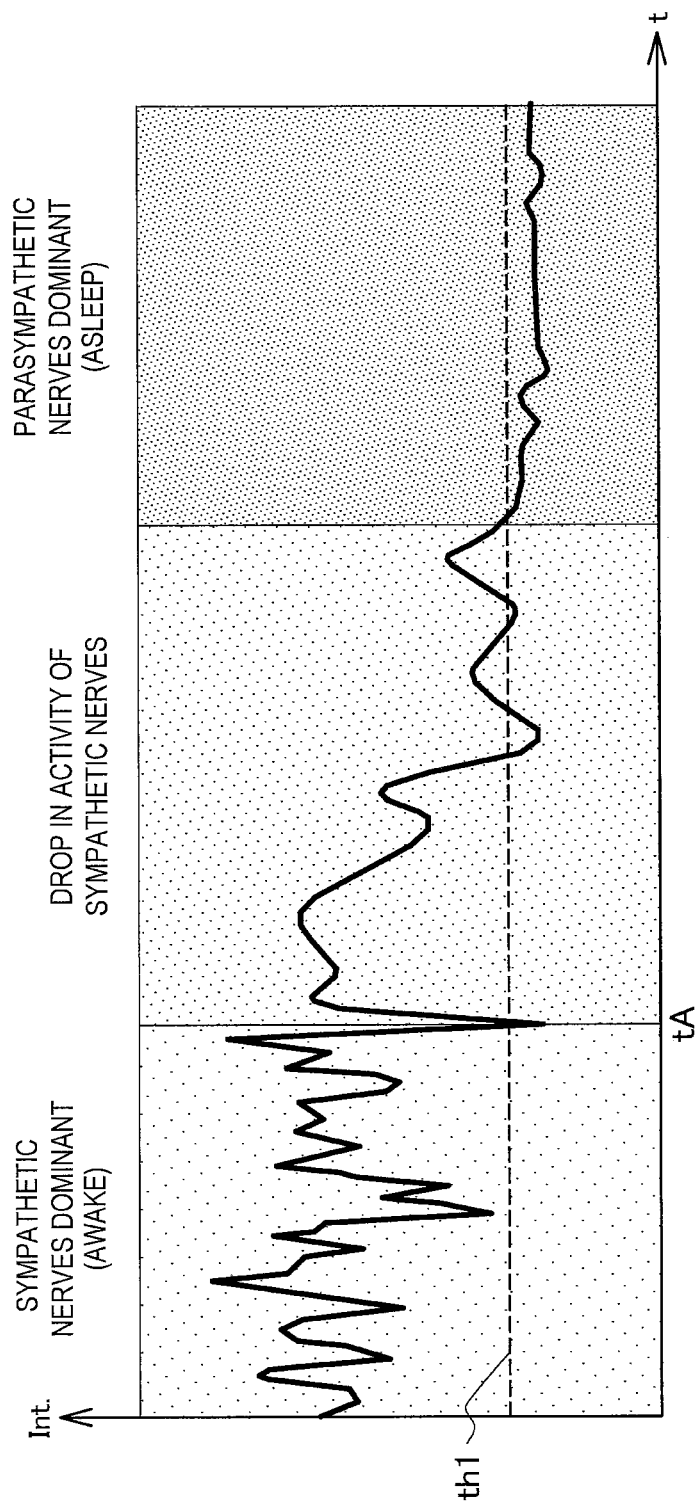
FIG. 19 is a diagram illustrating an example of a sleepiness detection process using an estimation result of the activity in the sympathetic nerves.

FIGS. 18 to 19 are diagrams for explaining a second applied example of the information processing system 1 according to the present embodiment. FIG. 18 is a diagram illustrating an example of an application situation of the present applied example. Also, FIG. 19 is a diagram illustrating an example of a sleepiness detection process using an estimation result of the activity in the sympathetic nerves. Note that the sleepiness detection process may be executed by the output control section 230 according to the present embodiment, for example.

Referring to FIG. 18, a user U3 is driving an automobile, and is operating a steering wheel 101. The perspiration sensor 11 is provided in a grip portion of the steering wheel 101. The biological sensor 12 or the like additionally may be provided in the grip portion. In this case, the control section 20, the communication section 21, and the storage section 22 of the information processing apparatus 10 may be realized by an engine control unit (ECU) of the automobile, a microprocessor provided separately from the ECU, or the like, for example. Additionally, the tracking sensor 13 and the environmental sensor 30 may be realized by any of various sensors provided in the automobile, for example. For example, the sensor may also be a tachometer, an acceleration sensor, a speed sensor, an accelerator pedal sensor, a brake sensor, a pressure sensor, a steering angle sensor, an illuminance sensor, a barometric pressure sensor, an inter-vehicle distance sensor, a monitoring camera, or the like. Also, as illustrated in FIG. 18, an alarm 140 may be provided in the cabin of the automobile. The alarm 140 is an example of the input/output device 14.

As illustrated in FIG. 18, when the user U3 is driving by gripping the steering wheel 101, the information processing system 1 estimates the activity in the sympathetic nerves of the user U3, and uses the estimation result to detect the sleepiness of the user U3. Referring to FIG. 19, a graph of strength indicating the activity in the sympathetic nerves is illustrated. The strength is a value according to the result of estimating the activity in the sympathetic nerves by the information processing apparatus 10. In the case in which the activity in the sympathetic nerves is dominant (that is, the user is awake), it is demonstrated that the strength is relatively high, and in addition, there is large oscillation of the strength. On the other hand, when the activity in the sympathetic nerves falls, the strength falls while the frequency of the oscillation of the strength also falls. Additionally, in the case in which the activity in the parasympathetic nerves becomes dominant (that is, the user is asleep), it is demonstrated that the strength falls below a predetermined threshold value (in FIG. 19, the threshold value th1), and in addition, little to no oscillation of the strength occurs.

Utilizing the above, in the case of determining that the strength has fallen below the threshold value th1, or that the frequency of change in the strength has fallen below a certain standard, the information processing system 1 outputs encouragement to keep the user awake. For example, in FIG. 19, since the strength falls below the threshold value th1 at the time tA, the information processing system 1 emits an alarm at the user U3 by the alarm 140. With this arrangement, the sleepy user U3 can be encouraged to stay awake.

Particularly, the information processing system 1 according to the present embodiment processes the perspiration data acquired by the perspiration sensor 11, and controls the output based on the estimation result of the activity in the autonomic nerves obtained as a result of the processing. The latency of mental perspiration is approximately several seconds as illustrated above, and a reaction is seen sooner than other effectors. Consequently, the information processing system 1 according to the present embodiment is capable of estimating the activity in the autonomic nerves of the user in real time. In so doing, like the second applied example described above, when driving a vehicle or the like, the occurrence of a serious accident or disaster due to a momentary lag in the judgment of a sleepy user can be prevented.

Also, by combining sensor data obtained from another sensor, such as automobile position information, with the estimation result of the activity in the sympathetic nerves of the user, it also becomes possible to determine the cause of the lapse in the user's concentration while driving the vehicle. For example, by checking the position information, speed, travel direction, and the like of the automobile against times when the activity in the sympathetic nerves of the user falls, locations on roads where accidents are likely to occur can be specified. In addition, the estimation result based on the perspiration data and the other sensor data may be accumulated appropriately in a shared database, for example. With this arrangement, it is not only possible to share locations on roads where accidents are likely to occur, but also investigate features shared in common among roads where accidents are likely to occur.

Note that in FIG. 18, the alarm 140 is provided as an example of the input/output device 14 for outputting to the user according to the estimation result, but the present technology is not limited to such an example. For example, the output to the user U3 may also be a change in the wind force or set temperature of an air conditioner provided in the automobile, an electrical stimulus imparted to the user U3 through the steering wheel 101, or the like. In addition, the output may also be control that adjusts the resistance of the accelerator or brake pedal that the user U3 steps on. Insofar as the output mode is able to encourage the wakefulness of the user U3 and ensure the safety of the user U3, any type of output apparatus may be applied as the input/output device 14.

The above describes the second applied example of the information processing system 1 according to the present embodiment. Note that the information processing system 1 is not limited to uses for promoting the wakefulness of a user who performs work where safety is demanded, such as driving an automobile as illustrated in the present applied example. For example, the present technology may also be used to make a user fall asleep and wake up at suitable timings. Specifically, the information processing system 1 may encourage a user to fall asleep when it is estimated that the activity in the parasympathetic nerves of the user trying to fall asleep have become dominant, and around a scheduled wake time, the information processing system 1 may encourage the user to wake up when it is estimated that the activity in the sympathetic nerves of the sleeping user have become dominant With this arrangement, the user using the information processing system 1 is able to obtain comfortable sleep.

<3.3. Model Sharing>

In addition, the various models (noise model 41, extraction model 42, and activity estimation model 43) used in the processing section 210 of the information processing apparatus 10 according to the present embodiment may also be shared among multiple information processing apparatus.

Figure 20:
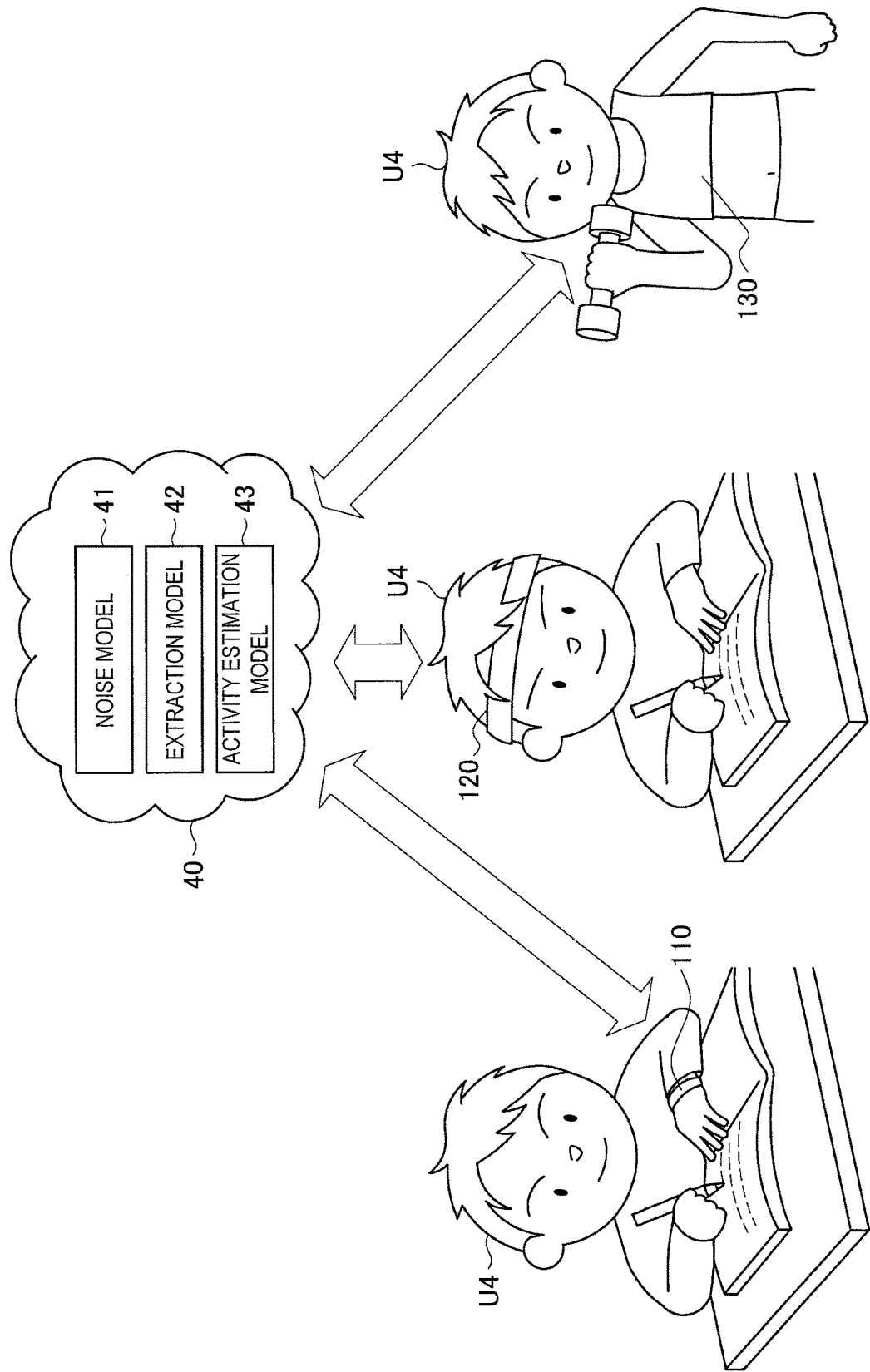
FIG. 20 is an outline diagram for explaining for explaining the shared usage of various models among multiple information processing apparatus.

FIG. 20 is an outline diagram for explaining for explaining the shared usage of various models among multiple information processing apparatus. As illustrated in FIG. 20, a user U4 possesses a wristwatch-style device 110, a hair band-style device 120, and a wearable device 130 in the mode of sportswear (for example, at least the perspiration sensor 11 is provided at a site corresponding to an armpit), and uses these devices appropriately depending on the situation. The wristwatch-style device 110, the hair band-style device 120, and the wearable device 130 are provided with at least the perspiration sensor 11, and are included as part of the information processing system 1.

The properties of the mental perspiration of a user are fixed regardless of the type of work that the user performs. Consequently, by sharing and using the various models stored in the server 40, even if the type of device is different, processing specialized for the user may be executed. In other words, regardless of the device type and the device usage frequency, the accuracy of the estimation result of the activity in the sympathetic nerves of the user can be kept high.

Also, depending on the site on the body, the degree of detection of mental perspiration is different. For example, compared to the wrists, mental perspiration may be detected more noticeably on the palms and the forehead. On the other hand, during daily life, the wrists are more suitable as the wear site or attachment site of the information processing apparatus (perspiration sensor) compared to the palms and the forehead. For this reason, in the case of using the various models described above shared among multiple information processing apparatus, the learning of the various models above may be executed using an information processing apparatus (perspiration sensor) worn on or attached to the palms or the forehead. Additionally, the various models constructed by learning may be applied to an information processing apparatus worn on or attached to the wrists. With this arrangement, compared to an information processing apparatus simply worn on or attached to the wrists only, it becomes possible to execute more accurate processes.

Note that the sharing of various models described above is described as relating to a specific user, but the present technology it not limited to such an example. For example, the sharing of various models described above may also be models shared by multiple users who use the information processing apparatus 10 according to the present embodiment. With this arrangement, since feedback for the various models is provided from the multiple users, general-purpose models can be constructed. Consequently, from the initial stages it becomes possible to raise the accuracy of estimating the activity in the sympathetic nerves of a user who starts to use the information processing apparatus 10.

The above describes applied examples of the information processing system 1 according to the present embodiment.

<<4. Hardware Configuration Example>>

Figure 21:
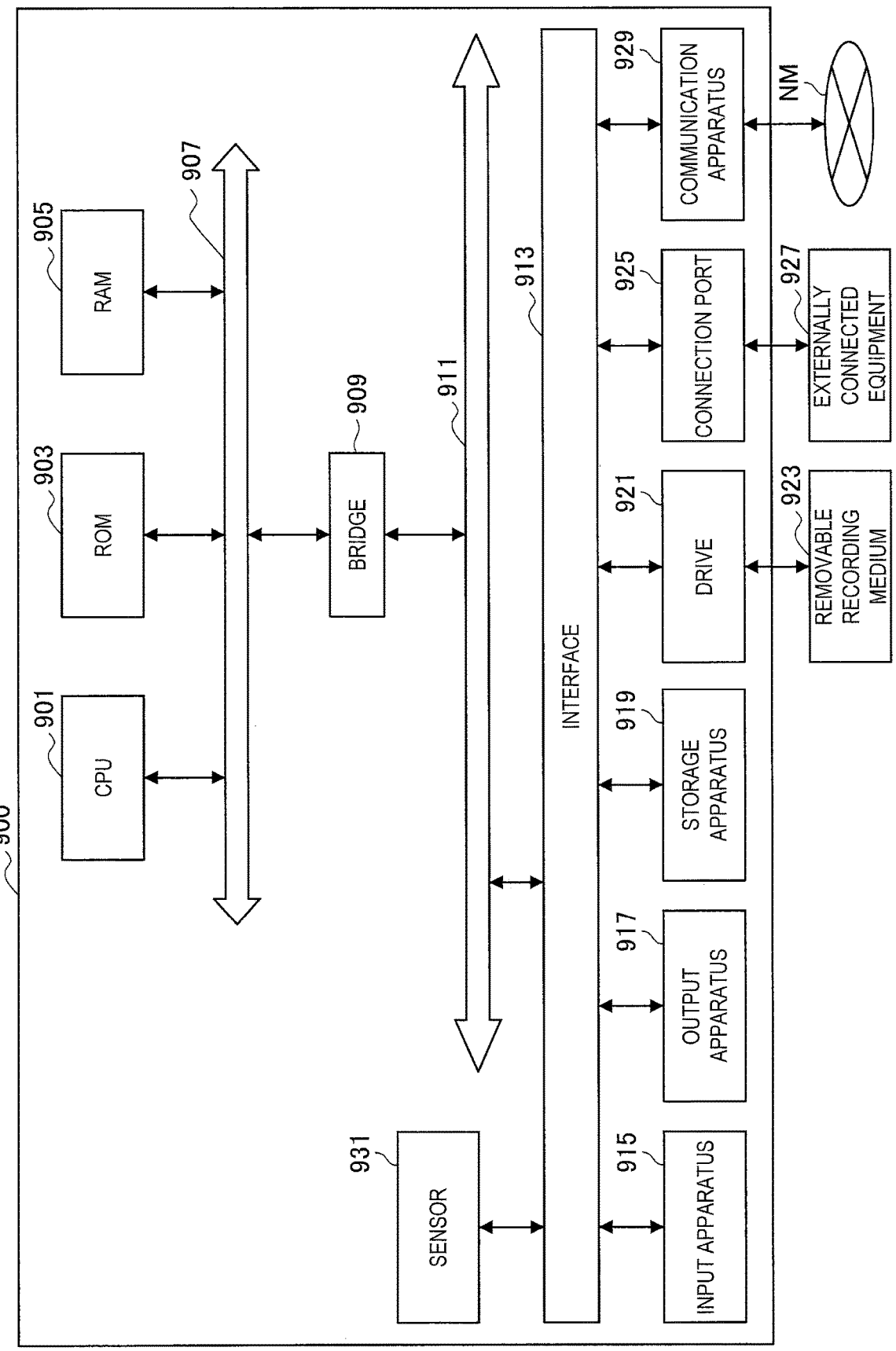
FIG. 21 is a block diagram illustrating an exemplary hardware configuration of the information processing apparatus according to an embodiment of the present disclosure.

Next, the hardware configuration of an information processing apparatus 900 according to an embodiment of the present disclosure is described with reference to FIG. 21. FIG. 21 is a block diagram illustrating a hardware configuration example of the information processing apparatus 900 according to an embodiment of the present disclosure. The illustrated information processing apparatus 900 may realize the information processing apparatus in the foregoing embodiment, for example.

The information processing apparatus 900 includes a central processing unit (CPU) 901, read-only memory (ROM) 903, and random-access memory (RAM) 905. In addition, the information processing apparatus 900 may include a host bus 907, a bridge 909, an external bus 911, an interface 913, an input apparatus 915, an output apparatus 917, a storage apparatus 919, a drive 921, a connection port 925, a communication apparatus 929, and a sensor 931. In conjunction with, or in place of, the CPU 901, the information processing apparatus 900 may have a processing circuit called a digital signal processor (DSP) or application specific integrated circuit (ASIC).

The CPU 901 functions as an arithmetic processing unit and a control unit, and controls the whole operation in the information processing apparatus 900 or a part thereof in accordance with various programs recorded in the ROM 903, the RAM 905, the storage apparatus 919, or a removable recording medium 923. The ROM 903 stores programs, operation parameters, or the like used by the CPU 901. The RAM 905 temporarily stores programs used in the execution by the CPU 901, parameters that vary as appropriate in the execution, or the like. For example, the CPU 901, the ROM 903, and the RAM 905 may realize the functions of the control section 20 in the foregoing embodiment. The CPU 901, the ROM 903, and the RAM 905 are connected with each other via the host bus 907 that includes an internal bus such as a CPU bus. Furthermore, the host bus 907 is connected to the external bus 911 such as peripheral component interconnect/interface (PCI) bus via the bridge 909.

The input apparatus 915 is, in one example, an apparatus operated by a user, such as a mouse, a keyboard, a touch panel, a button, a switch, and a lever. The input apparatus 915 may be, in one example, a remote control apparatus using infrared rays or other radio waves, or may be externally connected equipment 927 such as a cellular phone that supports the operation of the information processing apparatus 900. The input apparatus 915 includes an input control circuit that generates an input signal on the basis of the information input by the user and outputs it to the CPU 901. The user operates the input apparatus 915 to input various data to the information processing apparatus 900 and to instruct the information processing apparatus 900 to perform a processing operation.

The output apparatus 917 includes an apparatus capable of notifying visually or audibly the user of the acquired information. The output apparatus 917 may be a display apparatus such as a liquid crystal display (LCD), a plasma display panel (PDP), and an organic electro-luminescence display (OELD), an audio output apparatus such as a speaker and a headphone, as well as printer apparatus or the like. The output apparatus 917 outputs the result obtained by the processing of the information processing apparatus 900 as a video such as a text or an image, or outputs it as audio such as a speech or sound. Note that the input apparatus 915 and the output apparatus 917 may realize the functions of the input/output device 14 in the foregoing embodiment.

The storage apparatus 919 is a data storage apparatus configured as an example of a storage portion of the information processing apparatus 900. The storage apparatus 919 includes, in one example, a magnetic storage unit device such as hard disk drive (HDD), a semiconductor storage device, an optical storage device, and a magneto-optical storage device. The storage apparatus 919 stores programs executed by the CPU 901, various data, various types of data obtained from the outside, and the like.

The drive 921 is a reader-writer for a removable recording medium 923 such as a magnetic disk, an optical disk, a magneto-optical disk, and a semiconductor memory, and is incorporated in the information processing apparatus 900 or externally attached thereto. The drive 921 reads the information recorded on the loaded removable recording medium 923 and outputs it to the RAM 905. In addition, the drive 921 writes a record in the loaded removable recording medium 923. At least one of the storage apparatus 919, or the drive 921 and the removable recording medium 923 may realize the functions of the storage section 22 in the foregoing embodiment.

The connection port 925 is a port for directly connecting equipment to the information processing apparatus 900. The connection port 925 may be, in one example, a Universal Serial Bus (USB) port, an IEEE 1394 port, or a Small Computer Device Interface (SCSI) port. In addition, the connection port 925 may be, in one example, an RS-232C port, an optical audio terminal, or High-Definition Multimedia Interface (HDMI, registered trademark) port. The connection of the externally connected equipment 927 to the connection port 925 makes it possible to exchange various kinds of data between the information processing apparatus 900 and the externally connected equipment 927.

The communication apparatus 929 is, in one example, a communication interface including a communication device or the like, which is used to be connected to the communication network NW. The communication apparatus 929 may be, in one example, a communication card for wired or wireless local area network (LAN), Bluetooth (registered trademark), or wireless USB (WUSB). In addition, the communication apparatus 929 may be, in one example, a router for optical communication, a router for asymmetric digital subscriber line (ADSL), or a modem for various communications. The communication apparatus 929 transmits and receives signals or the like using a predetermined protocol such as TCP/IP, in one example, with the Internet or other communication equipment. In addition, the communication network NW connected to the communication apparatus 929 is a network connected by wire or wireless, and is, in one example, the Internet, home LAN, infrared communication, radio wave communication, satellite communication, or the like. Note that at least one of the connection port 925 and the communication apparatus 929 may realize the functions of the communication section 21 in the foregoing embodiment.

The above illustrates one example of a hardware configuration of the information processing apparatus 900.

<<5. Conclusion>>

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Note that the foregoing embodiment describes an example in which the target of application of the information processing system and the information processing apparatus is a user, that is, a human being, but the present technology is not limited to such an example. For example, the target of application of the information processing system and the information processing apparatus according to the foregoing embodiment may also be an animal, such as a domesticated animal or a pet. By applying such an information processing system and information processing apparatus to an animal, the level of stress imparted to the animal or the like can be grasped, making it easy to grasp the state of health of the animal.

Note that each of the steps in the processes of the information processing apparatus in this specification is not necessarily required to be processed in a time series following the sequence described as a flowchart. For example, each of the steps in the processes of the information processing apparatus may be processed in a sequence that differs from the sequence described herein as a flowchart, and furthermore may be processed in parallel.

Additionally, it is possible to create a computer program for causing hardware such as a CPU, ROM, and RAM built into an information processing apparatus to exhibit functions similar to each component of the information processing apparatus described above. In addition, a recording medium storing the computer program is also provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:
a processing section that executes a process including a correction process of specifying noise included in perspiration data acquired by a perspiration sensor on a basis of sensor data acquired by a different type of sensor than the perspiration sensor, and removing the noise from the perspiration data.

(2)

The information processing apparatus according to (1), in which
the processing section corrects the perspiration data using a noise model indicating a relationship between the noise and the perspiration data and/or the sensor data.

(3)

The information processing apparatus according to (2), in which
the noise model is generated by machine learning using the perspiration data, the sensor data acquired at a same time as the acquisition of the perspiration data, and a result of the process.

(4)

The information processing apparatus according to (2) or (3), in which
the noise model is a noise model associated with an individual corresponding to the perspiration data.

(5)

The information processing apparatus according to any one of (2) to (4), in which
the noise model is updated using feedback-related information acquired by user input with respect to a result of the process by the processing section.

(6)

The information processing apparatus according to any one of (1) to (5), in which
the process by the processing section additionally includes an extraction process of extracting mental perspiration data caused by mental perspiration from corrected perspiration data.

(7)

The information processing apparatus according to (6), in which
the processing section extracts the mental perspiration data using an extraction model indicating a relationship between a parameter used in the extraction process and the corrected perspiration data and/or the sensor data.

(8)

The information processing apparatus according to (6) or (7), in which
the process by the processing section additionally includes an estimation process of estimating activity in autonomic nerves of an individual corresponding to the perspiration data, on a basis of the extracted mental perspiration data.

(9)

The information processing apparatus according to (8), in which
the processing section estimates the activity in the autonomic nerves on a basis of a time-series distribution of the mental perspiration data.

(10)

The information processing apparatus according to (8) or (9), in which
the processing section estimates the activity in the autonomic nerves of the individual corresponding to the perspiration data by using an activity estimation model indicating a relationship between a parameter used in the estimation process and the mental perspiration data and/or the sensor data.

(11)

The information processing apparatus according to any one of (8) to (10), in which
the extraction process includes a process of additionally extracting thermal perspiration data caused by thermal perspiration from the corrected perspiration data, and
the estimation process includes a process of estimating the activity in the autonomic nerves of the individual corresponding to the perspiration data by using the extracted thermal perspiration data.

(12)

The information processing apparatus according to any one of (8) to (11), in which
the activity in the autonomic nerves includes activity in sympathetic nerves.

(13)

The information processing apparatus according to any one of (8) to (12), further including:
an output control section that controls an output according to a result of estimating the activity in the autonomic nerves.

(14)

The information processing apparatus according to any one of (1) to (13), in which
the processing section executes the process on a basis of the sensor data acquired at a same time as the acquisition of the perspiration data.

(15)

The information processing apparatus according to any one of (1) to (14), further including:
a context acquisition section that acquires context related to an individual on whom the perspiration sensor is worn or attached, in which
the processing section executes the process by additionally using the context.

(16)

The information processing apparatus according to any one of (1) to (15), in which
the different type of sensor than the perspiration sensor includes at least one sensor worn on or attached to an individual.

(17)

The information processing apparatus according to (16), in which
the sensor worn on or attached to the individual includes a biological sensor that detects biological information about the individual, and/or a tracking sensor that detects a motion of the individual.

(18)

The information processing apparatus according to any one of (1) to (17), in which
the different type of sensor than the perspiration sensor includes at least one sensor that acquires environmental information related to a predetermined space.

(19)

An information processing method, executed by a processor, including:
acquiring perspiration data acquired by a perspiration sensor; and
specifying noise included in the perspiration data on a basis of sensor data acquired by a different type of sensor than the perspiration sensor, and removing the noise from the perspiration data.

(20)

A program causing a computer to function as:
a processing section that executes a process including a correction process of specifying noise included in perspiration data acquired by a perspiration sensor on a basis of sensor data acquired by a different type of sensor than the perspiration sensor, and removing the noise from the perspiration data.

REFERENCE SIGNS LIST 1 information processing system
10 information processing apparatus
11 perspiration sensor
12 biological sensor
13 tracking sensor
14 input/output device
20 control section
21 communication section
22 storage section
30 environmental sensor
40 server
41 noise model
42 extraction model
43 activity estimation model
210 processing section
211 correction section
212 extraction section
213 estimation section
220 context acquisition section
230 output control section
240 feedback section

The invention claimed is:
1. An information processing apparatus, comprising:
a processing section configured to:
acquire perspiration data corresponding to an individual from a perspiration sensor and sensor data from a specific sensor different from the perspiration sensor, wherein
the perspiration data includes thermal perspiration data and mental perspiration data,
the mental perspiration data corresponds to mental perspiration that is based on an activity in autonomic nerves of the individual, and
the thermal perspiration data corresponds to thermal perspiration different from the mental perspiration;
execute a correction process to specify noise in the perspiration data,
wherein the noise in the perspiration data is specified based on a noise model that indicates a relationship between the noise and at least one of the perspiration data or the sensor data;
remove the noise from the perspiration data to obtain corrected perspiration data;
extract the mental perspiration data from the corrected perspiration data;
estimate the activity in the autonomic nerves based on the extracted mental perspiration data;
acquire feedback-related information based on a user input,
wherein the user input is with respect to a result of the estimation of the activity in the autonomic nerves; and
update the noise model based on the acquired feedback-related information.

2. The information processing apparatus according to claim 1, wherein
the specific sensor acquires the sensor data at a same time as an acquisition of the perspiration data by the perspiration sensor, and
the noise model is generated by machine learning based on the perspiration data, the sensor data, and a result of the execution of the correction process.

3. The information processing apparatus according to claim 1, wherein the noise model is associated with the individual corresponding to the perspiration data.

4. The information processing apparatus according to claim 1, wherein
the processing section is further configured to extract the mental perspiration data based on an extraction model, and
the extraction model indicates a relationship between:
a parameter of the extraction of the mental perspiration data, and
at least one of the corrected perspiration data or the sensor data.

5. The information processing apparatus according to claim 1, wherein the processing section is further configured to estimate the activity in the autonomic nerves based on a time-series distribution of the mental perspiration data.

6. The information processing apparatus according to claim 1, wherein
the processing section is further configured to estimate the activity in the autonomic nerves of the individual based on an activity estimation model, and
the activity estimation model indicates a relationship between:
a parameter of the estimation of the activity, and
at least one of the mental perspiration data or the sensor data.

7. The information processing apparatus according to claim 1, wherein the processing section is further configured to:
extract the thermal perspiration data from the corrected perspiration data, and
estimate the activity in the autonomic nerves of the individual based on the extracted thermal perspiration data.

8. The information processing apparatus according to claim 1, wherein the activity in the autonomic nerves includes an activity in sympathetic nerves.

9. The information processing apparatus according to claim 1, further comprising an output control section configured to control an output based on the result of the estimation of the activity in the autonomic nerves.

10. The information processing apparatus according to claim 1, wherein the sensor data is acquired by the specific sensor at a same time as an acquisition of the perspiration data by the perspiration sensor.

11. The information processing apparatus according to claim 1, further comprising a context acquisition section configured to acquire context information related to the individual, wherein
the perspiration sensor is at least one of wearable by the individual or attachable to the individual, and
the processing section is further configured to execute the correction process based on the context information.

12. The information processing apparatus according to claim 1, wherein the specific sensor different from the perspiration sensor is at least one of wearable by the individual or attachable to the individual.

13. The information processing apparatus according to claim 12, wherein the specific sensor includes at least one of:
a biological sensor that detects biological information of the individual, or
a tracking sensor that detects a motion of the individual.

14. The information processing apparatus according to claim 1, wherein the specific sensor different from the perspiration sensor acquires environmental information related to a space.

15. An information processing method, comprising:
acquiring perspiration data corresponding to an individual from a perspiration sensor and sensor data from a specific sensor different from the perspiration sensor, wherein
the perspiration data includes thermal perspiration data and mental perspiration data,
the mental perspiration data corresponds to mental perspiration that is based on an activity in autonomic nerves of the individual, and
the thermal perspiration data corresponds to thermal perspiration different from the mental perspiration;
executing a correction process to specify noise in the perspiration data,
wherein the noise in the perspiration data is specified based on a noise model that indicates a relationship between the noise and at least one of the perspiration data or the sensor data;
removing the noise from the perspiration data to obtain corrected perspiration data;
extracting the mental perspiration data from the corrected perspiration data;
estimating the activity in the autonomic nerves based on the extracted mental perspiration data;
acquiring feedback-related information based on a user input,
wherein the user input is with respect to a result of the estimation of the activity in the autonomic nerves; and
updating the noise model based on the acquired feedback-related information.

16. A non-transitory computer-readable medium having stored thereon computer-executable instructions, which when executed by a computer, cause the computer to execute operations, the operations comprising:
acquiring perspiration data corresponding to an individual from a perspiration sensor and sensor data from a specific sensor different from the perspiration sensor, wherein
the perspiration data includes thermal perspiration data and mental perspiration data,
the mental perspiration data corresponds to mental perspiration that is based on an activity in autonomic nerves of the individual, and
the thermal perspiration data corresponds to thermal perspiration different from the mental perspiration;
executing a correction process to specify noise in the perspiration data,
wherein the noise in the perspiration data is specified based on a noise model that indicates a relationship between the noise and at least one of the perspiration data or the sensor data;
removing the noise from the perspiration data to obtain corrected perspiration data;
extracting the mental perspiration data from the corrected perspiration data;
estimating the activity in the autonomic nerves based on the extracted mental perspiration data;
acquiring feedback-related information based on a user input,
wherein the user input is with respect to a result of the estimation of the activity in the autonomic nerves; and
updating the noise model based on the acquired feedback-related information.

* * * * *